US012582812B2

(12) United States Patent
Davis

(10) Patent No.: US 12,582,812 B2
(45) Date of Patent: Mar. 24, 2026

(54) SELECTABLY LOCKING MEDICAL COUPLING

(71) Applicant: Benjamin Martin Davis, Woodstock, GA (US)

(72) Inventor: Benjamin Martin Davis, Woodstock, GA (US)

(73) Assignee: Adavation LLC, Woodstock, GA (US)

( * ) Notice: Subject to any disclaimer, the term of this patent is extended or adjusted under 35 U.S.C. 154(b) by 0 days.

(21) Appl. No.: 18/956,351

(22) Filed: Nov. 22, 2024

(65) Prior Publication Data

US 2025/0161650 A1     May 22, 2025

Related U.S. Application Data

(60) Provisional application No. 63/602,071, filed on Nov. 22, 2023.

(51) Int. Cl.
*F16L 37/24*          (2006.01)
*A61M 39/10*          (2006.01)

(52) U.S. Cl.
CPC . *A61M 39/1011* (2013.01); *A61M 2039/1038* (2013.01); *A61M 2205/583* (2013.01)

(58) Field of Classification Search
CPC ......... F16L 15/00; F16L 37/24; F16L 37/244; F16L 37/2445; F16L 37/248;
(Continued)

(56) References Cited

U.S. PATENT DOCUMENTS 2,290,348 A     7/1942   Moule
2,434,612 A     1/1948   Hamiel
(Continued)

FOREIGN PATENT DOCUMENTS

CN          112208932 A      1/2021
DE          20302788 U1      6/2004
(Continued)

OTHER PUBLICATIONS

Baxa (Baxter) RAPIDFILL Connector; 1 pg; Last retrieval date Jan. 13, 2023.
(Continued)

*Primary Examiner* — Aaron M Dunwoody
(74) *Attorney, Agent, or Firm* — Perilla Knox & Hildebrandt LLP; Stephanie L. Davy-Jow

(57)          ABSTRACT
A male or female orientated medical tubing or syringe connector that can be selectably locked in a threaded configuration or a breakaway configuration. The male connector includes opposing threaded sections and opposing non-threaded sections. The opposing threaded sections allow for the male connector's fully or partially threaded female counterpart to be screwed into place on attachment and unscrewed on detachment. The opposing unthreaded sections of the male connector allow for its partially threaded female counterpart to be engaged via a friction fit connection that does not require a screwing action. The male connector's opposing unthreaded sections also allows for its partially threaded female counterpart to be disengaged via a pulling force in the opposite direction of the male connector, which does not require an unscrewing action. This "breakaway" functionality helps to prevent patient harm if the patient's tubing becomes snagged.

16 Claims, 15 Drawing Sheets

(58) Field of Classification Search
CPC .. F16L 37/252; F16L 37/107; A61M 39/1011; A61M 2039/1038; A61M 2039/1044; A61M 2039/1077; A61M 2039/1033; A61M 2039/1016
USPC ...................................... 285/34, 30, 31, 391
See application file for complete search history.

(56) References Cited

U.S. PATENT DOCUMENTS

| | | | |
|---|---|---|---|
| 2,783,908 A | 3/1957 | John | |
| 3,307,752 A | 3/1967 | Anderson | |
| 3,545,637 A | 12/1970 | Barr | |
| 3,645,262 A | 2/1972 | Harrigan | |
| 3,735,888 A | 5/1973 | Jacko | |
| 4,076,285 A * | 2/1978 | Martinez ............... F16L 37/252 | |
| | | | 285/376 |
| 4,230,112 A | 10/1980 | Smith | |
| 4,303,071 A | 12/1981 | Smith | |
| 4,317,448 A | 3/1982 | Smith | |
| 4,493,348 A | 1/1985 | Lemmons | |
| 4,508,236 A | 4/1985 | Keilman et al. | |
| 4,515,752 A | 5/1985 | Miramanda | |
| 4,573,506 A | 3/1986 | Paoletti | |
| 4,685,173 A | 8/1987 | Pavur | |
| 4,883,483 A | 11/1989 | Lindmayer | |
| 4,944,736 A | 7/1990 | Holtz | |
| 5,060,812 A | 10/1991 | Ogle, II | |
| 5,088,612 A | 2/1992 | Storar et al. | |
| 5,232,109 A | 8/1993 | Tirrell et al. | |
| 5,238,130 A | 8/1993 | Marques et al. | |
| 5,356,406 A | 10/1994 | Schraga | |
| 5,429,256 A | 7/1995 | Kestenbaum | |
| 5,454,409 A | 10/1995 | McAffer et al. | |
| 5,454,805 A | 10/1995 | Brony | |
| 5,484,070 A | 1/1996 | Graham | |
| 5,573,525 A | 11/1996 | Watson et al. | |
| 5,598,939 A | 2/1997 | Watson et al. | |
| 5,620,434 A | 4/1997 | Brony | |
| 5,688,254 A | 11/1997 | Lopez et al. | |
| D398,060 S | 9/1998 | Brown | |
| 5,902,298 A | 5/1999 | Niedospial, Jr. et al. | |
| 5,921,419 A | 7/1999 | Niedospial, Jr. et al. | |
| 5,931,828 A | 8/1999 | Durkee | |
| 5,971,181 A | 10/1999 | Niedospial, Jr. et al. | |
| 6,056,135 A | 5/2000 | Widman | |
| D528,910 S | 9/2006 | Kingsley | |
| D530,200 S | 10/2006 | Kingsley | |
| 7,128,228 B2 | 10/2006 | Collins | |
| 7,681,750 B2 | 3/2010 | Jackel | |
| 7,717,281 B2 | 5/2010 | Baudin | |
| D627,899 S | 11/2010 | Cofie | |
| 7,832,581 B2 | 11/2010 | Van Cromvoirt | |
| D630,732 S | 1/2011 | Lev et al. | |
| 7,985,205 B2 | 7/2011 | Adams | |
| D644,618 S | 9/2011 | Morihira | |
| 8,100,854 B2 | 1/2012 | Vogelin et al. | |
| D674,277 S | 1/2013 | Hanson et al. | |
| 8,459,312 B2 | 6/2013 | Manera et al. | |
| 8,464,882 B2 | 6/2013 | Tirosh | |
| D686,339 S | 7/2013 | Shima et al. | |
| 8,551,068 B2 | 10/2013 | Kyle et al. | |
| D693,923 S | 11/2013 | Hernandez et al. | |
| D706,135 S | 6/2014 | Hutchison et al. | |
| 8,758,322 B2 | 6/2014 | McCoy et al. | |
| D714,142 S | 9/2014 | Hojo | |
| D716,636 S | 11/2014 | McDonald | |
| D723,181 S | 2/2015 | Kawamura | |
| 8,950,608 B2 | 2/2015 | DeJong et al. | |
| D725,284 S | 3/2015 | Karlsson et al. | |
| 8,967,405 B2 | 3/2015 | Morrone | |
| D731,065 S | 6/2015 | Winter | |
| D737,962 S | 9/2015 | Schultz | |
| 9,126,029 B2 | 9/2015 | Fangrow et al. | |
| 9,156,569 B2 | 10/2015 | Vassallo et al. | |
| 9,296,531 B2 | 3/2016 | Luzbetak et al. | |

| | | | |
|---|---|---|---|
| D756,200 S | 5/2016 | McDonald | |
| 9,345,639 B2 | 5/2016 | Ferrara | |
| 9,433,562 B2 | 9/2016 | Ingram et al. | |
| 10,058,481 B1 | 8/2018 | Russo | |
| 10,668,263 B2 | 6/2020 | Ingram et al. | |
| 10,857,068 B2 | 12/2020 | Davis et al. | |
| 11,166,876 B2 | 11/2021 | Davis et al. | |
| 2005/0258125 A1 | 11/2005 | Kiehne | |
| 2006/0217679 A1 | 9/2006 | Hanly et al. | |
| 2008/0015539 A1 | 1/2008 | Pieroni et al. | |
| 2009/0062775 A1 * | 3/2009 | Kitani ................ A61M 39/1011 | |
| | | | 604/539 |
| 2009/0230075 A1 | 9/2009 | Springer | |
| 2009/0321611 A1 | 12/2009 | Moberg | |
| 2010/0327010 A1 | 12/2010 | Manera et al. | |
| 2011/0054436 A1 | 3/2011 | Griffis et al. | |
| 2012/0103470 A1 | 5/2012 | Terwilliger et al. | |
| 2012/0104054 A1 | 5/2012 | Terwilliger et al. | |
| 2012/0216909 A1 | 8/2012 | Levy | |
| 2012/0289936 A1 | 11/2012 | Ingram et al. | |
| 2014/0246616 A1 | 9/2014 | Fangrow et al. | |
| 2014/0299568 A1 | 10/2014 | Browne et al. | |
| 2015/0126941 A1 | 5/2015 | Felts et al. | |
| 2015/0129535 A1 | 5/2015 | Morrone | |
| 2015/0238387 A1 | 8/2015 | Caetano | |
| 2015/0320638 A1 | 11/2015 | Becker et al. | |
| 2016/0015601 A1 | 1/2016 | Davidson | |
| 2016/0067147 A1 | 3/2016 | Davis et al. | |
| 2016/0159635 A1 | 6/2016 | Davis et al. | |
| 2016/0217679 A1 | 7/2016 | Mcnutt et al. | |
| 2016/0317393 A1 | 11/2016 | Davis et al. | |
| 2016/0367439 A1 | 12/2016 | Davis et al. | |
| 2017/0014616 A1 | 1/2017 | Davis et al. | |
| 2017/0239141 A1 | 8/2017 | Davis et al. | |
| 2018/0099791 A1 | 4/2018 | Doornbos et al. | |
| 2019/0105484 A1 | 4/2019 | Doornbos et al. | |

FOREIGN PATENT DOCUMENTS

| | | | |
|---|---|---|---|
| EP | 0960616 A2 | 12/1999 | |
| EP | 2959877 A | 12/2015 | |
| GB | 2379253 A | 3/2003 | |
| TW | M512003 U | 11/2015 | |
| WO | 9803210 A2 | 1/1998 | |
| WO | 9846278 A1 | 10/1998 | |
| WO | 9932155 A2 | 7/1999 | |
| WO | 02085429 A2 | 10/2002 | |
| WO | 2005065767 A2 | 7/2005 | |
| WO | 2005087127 A1 | 9/2005 | |
| WO | 2009068987 A1 | 6/2009 | |
| WO | 2012024370 A1 | 2/2012 | |
| WO | 2013081699 A2 | 6/2013 | |
| WO | 2014077670 A1 | 5/2014 | |
| WO | 2015146831 A1 | 10/2015 | |
| WO | 2016040126 A1 | 3/2016 | |
| WO | 2016089869 A1 | 6/2016 | |
| WO | 2018022631 A1 | 2/2018 | |

OTHER PUBLICATIONS

Baxa Adapta-Cap Bottle Adapter; 1 pg; Last retrieval date Jan. 13, 2023.
Baxter AdaptACap Bottle Adapter; 1 pg; Last retrieval date Jan. 13, 2023.
BioJect Needle-Free Vial Adapter; 1 pg; Last retrieval date Jan. 13, 2023.
CareFusion Universal Vented Vial Adapter; 2 pgs; 2013.
Comar Oral Syringe Bottle Adapters; 3 pgs; Last retrieval date Jan. 13, 2023.
GEDSA ENFit Pharmacy Resource Guide; 3 pgs; Last retrieval date Jan. 13, 2023.
ISO/FDIS 80369-1. (n.d.). International Organization for Standardization. Retrieved Nov. 12, 2024, from https://www.iso.org/standard/82071.html.
Iso-Med Press-In Bottle Adapters; 1 pg; Last retrieval date Jan. 13, 2023.

(56)          References Cited

OTHER PUBLICATIONS

Medela Breastmilk Transfer Lid; 1 pg; Last retrieval date Jan. 13, 2023.
Medicina ENFit Press in Adapter; 18 pgs; Last retrieval date Jan. 13, 2023.
Medi-Dose EPS Press-In Bottle Adapters; 1 pg; Last retrieval date Jan. 13, 2023.
Medispense Stepped Stopper; 1 pg; Last retrieval date Jan. 13, 2023.
NeoMed Closed System NeoBottle; 1 pg; Last retrieval date Jan. 13, 2023.
Oral Slip to Oral Ship Adapter, Health Care Logistics, Inc.; 1 pg; Last retrieval date Jan. 13, 2023.
PDG—The Packaging Design Group Sealsafe Press in Bottle Adapter (PIBA); 1 pg; Last retrieval date Jan. 13, 2023.
Specialty Medical Products Coupling (Item Code SMP-SCFF); Apr. 10, 2014; 1 pg.
Sterile Luer Lock to Oral Slip Adapter; Health Care Logistics, Inc.; 1 pg; Last retrieval date Jan. 13, 2023.
The Oley Foundation Resource Guide; 4 pgs; Last retrieval date Jan. 13, 2023.
Total Pharmacy Supply Bottle Adapter Plug; 1 pg; Last retrieval date Jan. 13, 2023.
Total Pharmacy Supply Universal Bottle Adapter; 1 pg; Last retrieval date Jan. 13, 2023.
Vygon Fluid Dispensing Connector; 1 pg; Last retrieval date Jan. 13, 2023.
WestPharma Vial Adapters; 2 pgs; 2014.

\* cited by examiner

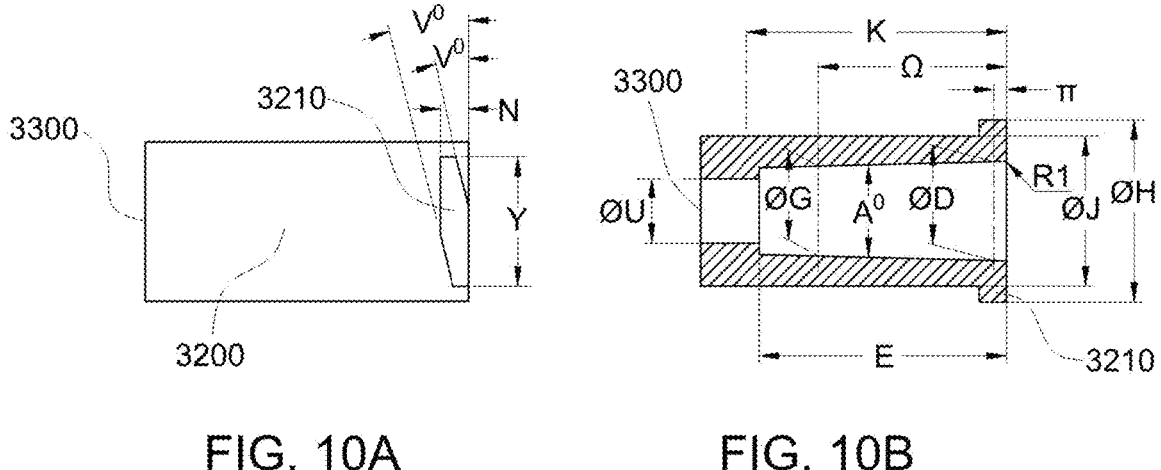
FIG. 10A                    FIG. 10B
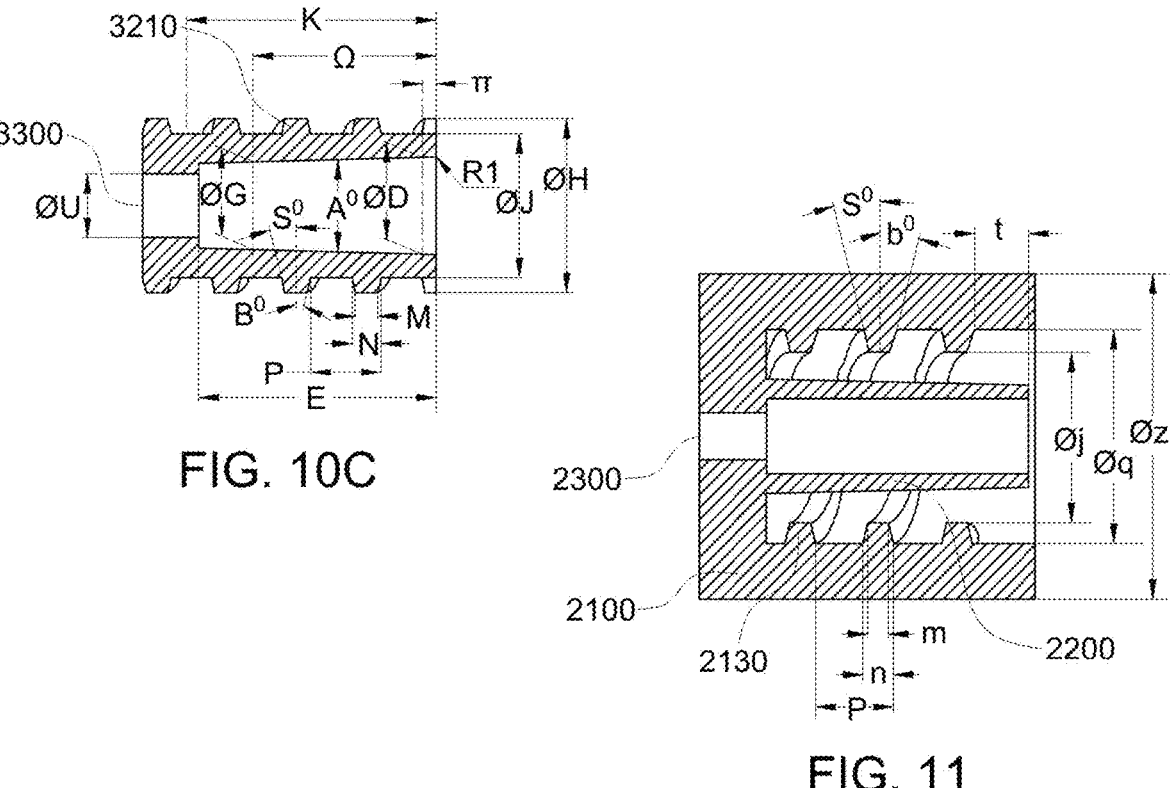
FIG. 10C
FIG. 11

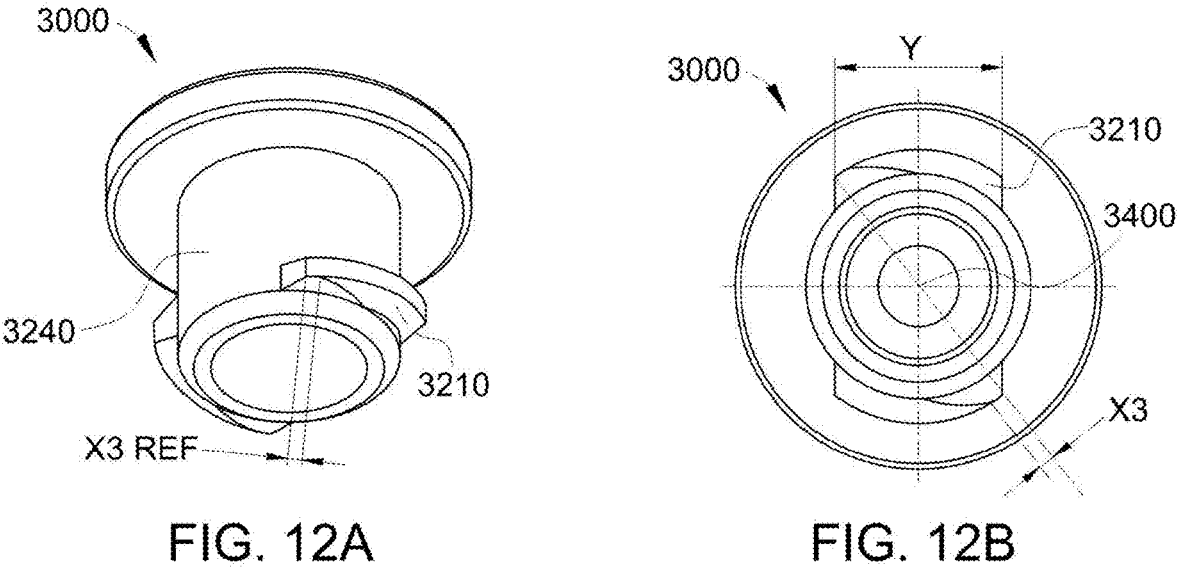
FIG. 12A
FIG. 12B
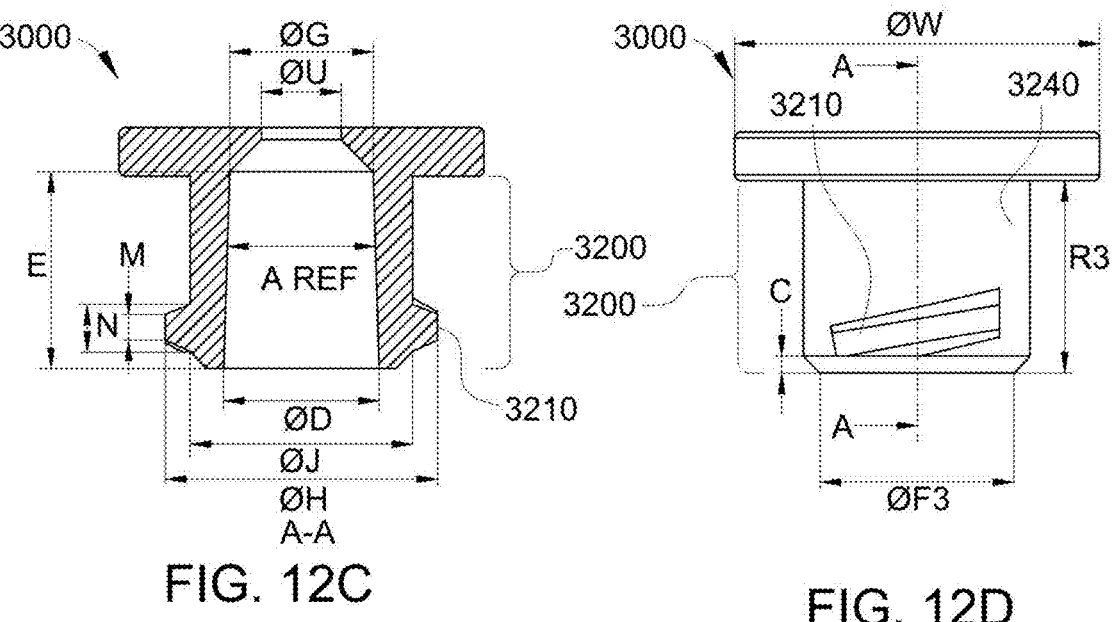
FIG. 12C
FIG. 12D

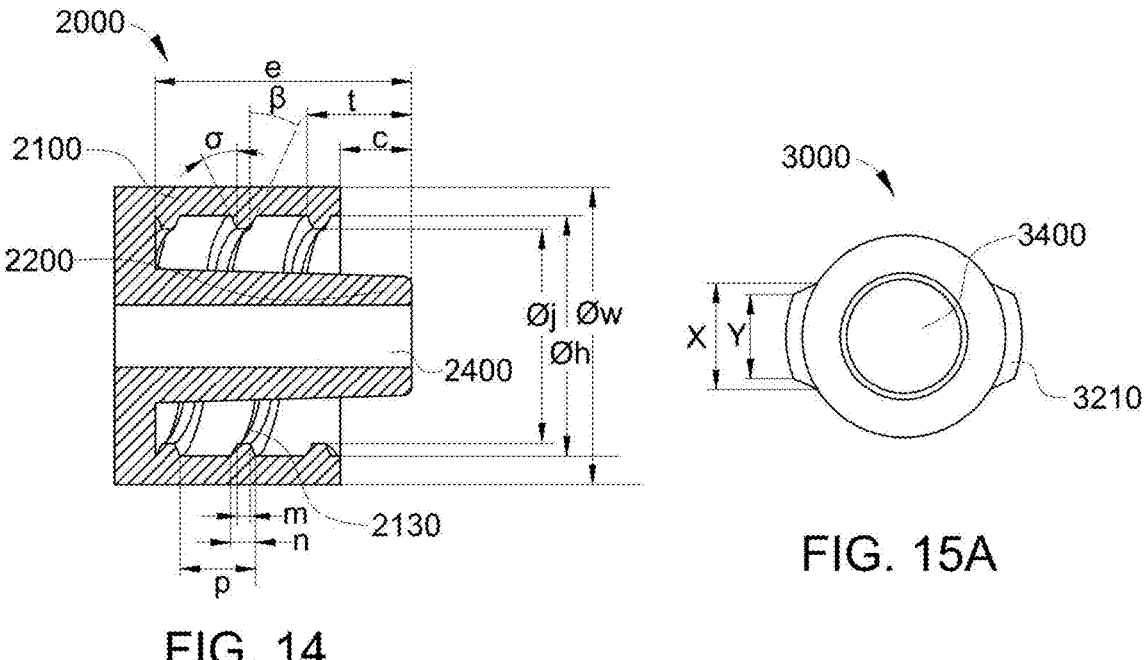
FIG. 14
FIG. 15A
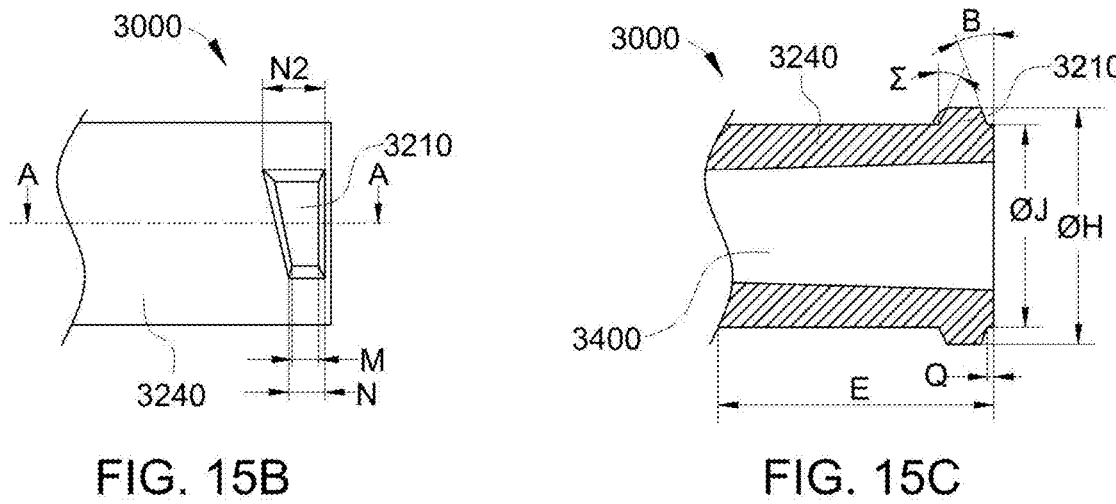
FIG. 15B
FIG. 15C

SELECTABLY LOCKING MEDICAL COUPLING

CROSS-REFERENCE TO RELATED APPLICATIONS

This application claims the benefit of U.S. Provisional Application No. 63/602,071, filed Nov. 22, 2023, the entire contents of which is hereby incorporated herein by reference.

TECHNICAL FIELD

The present invention relates generally to the field of medical small-bore tubing couplings or connectors that facilitate the transfer of fluids in applications such as enteral, intravascular, neuraxial, respiratory, urinary, limb cuff inflation, and other applicable areas of therapy.

BACKGROUND

Various medical small-bore tubing connectors are used for the delivery of intravenous/intravascular medications and nutrition, enteral medications and nutrition, neuraxial/neural medications, and for other treatments in different bodily systems or areas of therapy. Cross-application connections between these bodily systems are known as tubing misconnections and they often result in wrong route administration errors that can result in patient harm and death. For this reason, best practice guidelines call for dedicated connectors for each of these bodily systems. These guidelines, most notably the International Organization for Standardization (ISO) 80369 series of small-bore tubing connector standards, call for rigid connectors that are often specified to have threaded, locking configurations that screw together. The dimensions specified in these ISO standards were engineered to minimize the potential for different tubing applications to cross-connect/misconnect with incompatible areas of therapy. Additionally, the locking configuration of the connectors helps to prevent accidental tubing disconnections. However, there are circumstances under which a friction fit configuration is more desirable while still preventing cross-application connections.

It is to the provision of patient care and safety, clinical practice, and clinician, caregiver, and patient preference improvements to small-bore tubing connectors that the present invention is primarily directed.

SUMMARY

Embodiments of the present disclosure provide for selectably locking couplers, selectably locking male connectors, and selectably locking connector systems for use in medical fluid delivery. An embodiment of the present disclosure includes couplers for providing selectably locking coupling between a male and a female small bore medical connector. The coupler can include a body connecting a male end and a female end. The body can include an interior surface which contains opposing threaded sections alternating with unthreaded sections. The coupler can include an internal bore extending from the male end through the female end, with the male end including a nozzle having a tapered end. The female end can be positioned at an opposing side of the body from the male connector. The male end couples with and is dimensionally compatible with a standard female connector. The female end couples with and is dimensionally compatible with a standard male connector. Each of the opposing unthreaded sections can have a width greater than or equal to a corresponding lug width of the standard female connector. When the coupler is coupled with both the standard female connector and the standard male connector in a first position in which the opposing threaded sections mate with the lugs of the standard female connector, the coupler forms a threadably locking connection. When the coupler is coupled with both the standard female connector and the standard male connector in a second position, the lugs of the standard female connector align with and slot into the unthreaded sections to form a breakaway connection. The coupler remains fluidly coupled when selecting between the first position and the second position or between the second position and the first position. The standard female connector and standard male connectors can be an International Organization for Standardization 80369 series (ISO)-compliant connector.

An embodiment of the present disclosure also includes a selectably locking male connector that can include a first connection end that connects to tubing, a syringe, or other device and a central nozzle at an opposing end from the first connection end. The connector can also include a body positioned between the first connection end and the central nozzle, where the body has an interior surface with opposing threaded sections alternating with opposing unthreaded sections, and a central bore extending from the first connection end through the central nozzle. The selectably locking male connector prevents tubing misconnections between body systems.

An embodiment of the present disclosure also includes a selectably locking connector system for fluid transfer. The system can include a male connector and a corresponding female connector. The male connector can include a first connection end, a central nozzle at a second end opposite the first connection end, a body positioned between the first connection end and the central nozzle, the body having an interior surface comprising opposing threaded sections alternating with opposing unthreaded sections, and a central bore extending from the first connection end through the central nozzle. The corresponding female connector can include a first connection end and a cylindrical body at a second end opposite the first connection end. The cylindrical body can include a female receiver and a central bore extending from the first connection end through the female receiver. The nozzle of the male connector is dimensionally compatible with the female receiver and the selectably locking male connector prevents tubing misconnections between body systems.

These and other aspects, features and advantages of the invention will be understood with reference to the drawing figures and detailed description herein and will be realized by means of the various elements and combinations particularly pointed out in the appended claims. It is to be understood that both the foregoing general description and the following brief description of the drawings and detailed description of example embodiments are explanatory of example embodiments of the invention, and are not restrictive of the invention, as claimed.

BRIEF DESCRIPTION OF THE DRAWINGS

For a more complete understanding of the embodiments and the advantages thereof, reference is now made to the following description, in conjunction with the accompanying figures briefly described as follows:

FIG. 1A is a side view showing the window; FIG. 1B is a perspective view; FIG. 1C is a side view rotated 90 degrees from FIG. 1A; FIG. 1D is a top view from the male end; and FIG. 1E is a bottom view from the female end.

FIG. 2A shows the coupler and the connectors in an exploded view of the breakaway position. FIG. 2B shows the coupler and the connectors engaged in a breakaway position. FIG. 2C is a cross-sectional view of FIG. 2B. FIG. 2D shows the coupler and the connectors in an exploded view of the threadably locked position. FIG. 2E shows the coupler and the connectors engaged in a threadably locked position. FIG. 2F is a cross-sectional view of FIG. 2D.

FIG. 3A shows a side perspective view with its opposing unthreaded sections and windows; FIG. 3B shows a view from the proximal end with its opposing threadless and opposing threaded sections; FIG. 3C shows a perspective view of the proximal end with its opposing threadless sections and windows and with its opposing threaded sections; and FIG. 3D shows a view of the male connector from FIG. 3C that has been rotated 90 degrees, showing its opposing faintly threaded sections that form a continuation of the normally threaded sections' threading, its windows, and its opposing normally threaded sections.

FIG. 4A shows a first perspective view of the proximal end having opposing threadless sections; FIG. 4B shows a proximal end view having opposing threadless and opposing threaded sections; FIG. 4C shows a side view having opposing threadless windows on opposing sides of the cylindrical body; and FIG. 4D shows a side view rotated 90 degrees from FIG. 4C, such that the opposing threadless widows are aligned and the nozzle is visible through the windows.

FIG. 5A shows a side view of a male connector (left) and partially threaded female connector (right) separate from one another in a friction, or breakaway, fitment orientation; FIG. 5B shows a side view of a female connector in a friction, or breakaway, fitment with a male connector, with this connection configuration being indicated by the visibility of the partial threads of the female connector being centered in the opposing threadless windows of the male connector, according to an example embodiment of the present invention. FIG. 5C is a cross-sectional view of the fitted connectors in FIG. 5B; FIG. 5D shows the same connectors, where the female connector is in a threaded, or locking, fitment orientation with the male connector; FIG. 5E shows a side view of a female connector in a threaded, or locking, fitment with a male connector, with this connection configuration being indicated by the absence of the partial threads of the female connector from the opposing threadless windows of the male connector, according to an example embodiment of the present invention.

FIG. 6A shows a side view and FIG. 6B shows a perspective view.

FIG. 7A shows a side view and FIG. 7B shows a perspective view.

FIG. 9A is a first perspective view; FIG. 9B is an overhead or end view.

FIGS. 10A and 10B are drawings of a standard partially threaded female connector compatible with ISO 80369-6 neuraxial connectors and FIG. 10C is cross-sectional view of a fully threaded female connector compatible with ISO 80369-6 neuraxial connectors, according to known embodiments. FIG. 10A shows an external view and FIG. 10B is a cross-sectional view.

FIG. 11 is a drawing in a cross-sectional view of a selectably locking male connector compatible with ISO 80369-6 neuraxial connectors, according to known embodiments.

FIGS. 12A-12D are drawings of a female ISO 80369-3 enteral connector, according to various known embodiments. FIG. 12A is a perspective view; FIG. 12B is a top view from the threaded end; FIG. 12C is a cross-sectional view; and FIG. 12D a side view.

FIG. 13A is a perspective view; FIG. 13B is a top view from the threaded end; FIG. 12C is a cross-sectional view; and FIG. 13D is a side view.

FIG. 14 is a drawing of a male ISO 80369-7 intravenous/intravascular connector, according to various known embodiments.

FIGS. 15A-15E are drawings of a female ISO 80369-7 intravenous connector, according to various known embodiments. FIG. 15A is a top view from the threaded end; FIG. 15B shows the partial thread angle; FIG. 15C is a cross-sectional view; FIG. 15D shows the fully threaded version; and FIG. 15E is a cross-section of FIG. 15E.

Figures 1A, 1B, 1C, 1D, 1E:
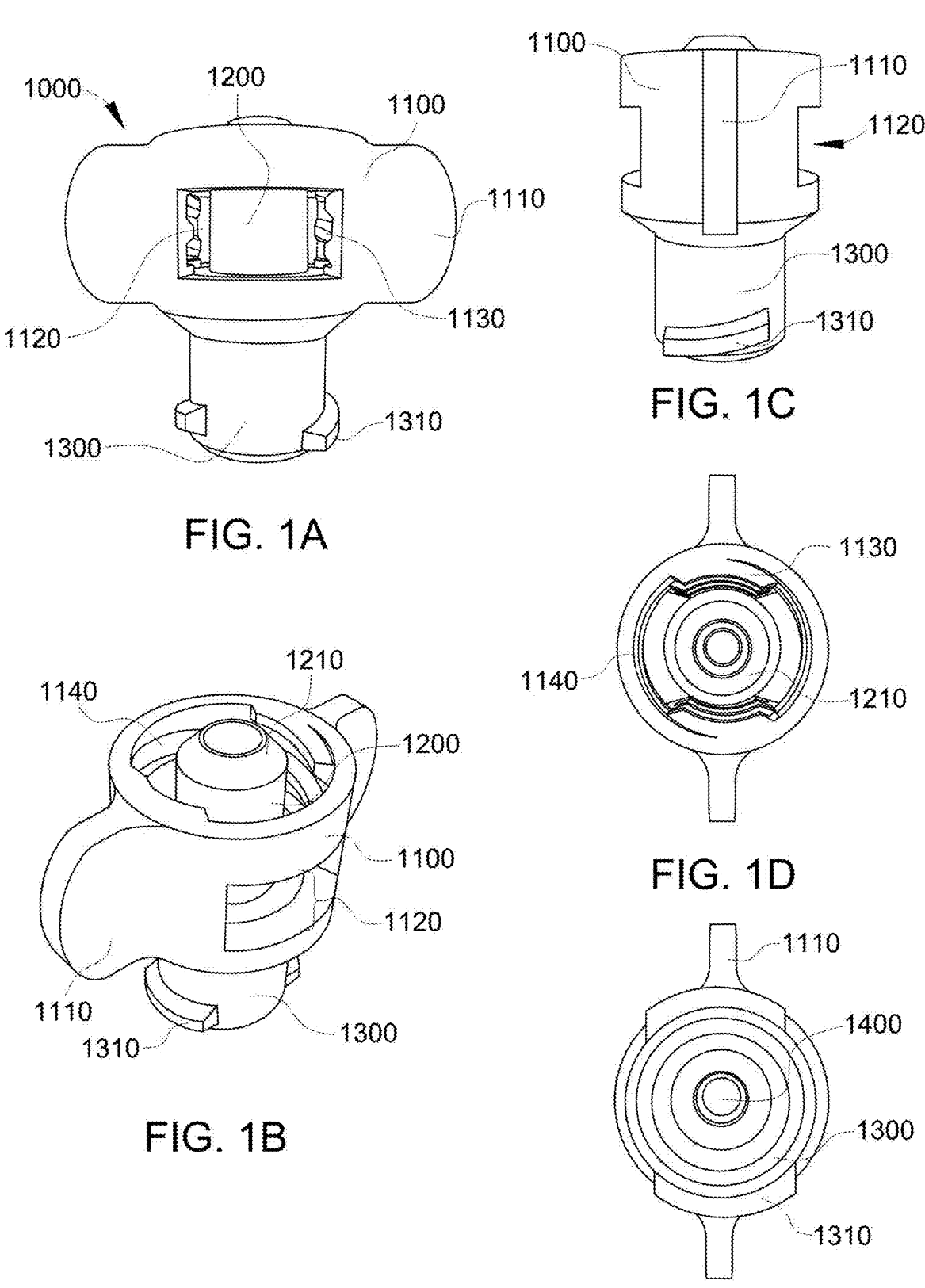
FIGS. 1A-1E are drawings of a coupler according to various example embodiments.

The drawings illustrate only example embodiments and are therefore not to be considered limiting of the scope described herein, as other equally effective embodiments are within the scope and spirit of this disclosure. The elements and features shown in the drawings are not necessarily drawn to scale, emphasis instead being placed upon clearly illustrating the principles of the embodiments. Additionally, certain dimensions may be exaggerated to help visually convey certain principles. In the drawings, similar reference numerals between figures designate like or corresponding, but not necessarily the same, elements.

DETAILED DESCRIPTION OF EXAMPLE EMBODIMENTS

The present invention may be understood more readily by reference to the following technical description of example embodiments taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Although the relative terms such as "on," "below," "upper," and "lower" are used in the specification to describe the relative relationship of one component to another component, these terms are used in this specification for convenience only, for example, as a direction in an example shown in the drawings. It should be understood that if the device is turned upside down, the "upper" component described above will become a "lower" component. When a structure is "on" another structure, it is possible that the structure is integrally formed on another structure, or that the structure is "directly" disposed on another structure, or that the structure is "indirectly" disposed on the other structure through other structures.

The terms "first," "second," etc. are used only as labels, rather than a limitation for a number of the objects. It is understood that if multiple components are shown, the components may be referred to as a "first" component, a "second" component, and so forth, to the extent applicable.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Definitions

Friction fit, also referred to as slip fit, press fit, interference fit, or cone and socket fitment, as used herein refers to a connection in which a male component inserts into a female component with straight pushing force and can be decoupled by the use of straight pulling force, which decoupling can be referred to as a, disconnection, connector separation, breakaway connection, or breakaway fitment.

Disconnection, separable connection, breakaway connection, or breakaway fitment, as used herein, refers to a friction fit connection which can be decoupled by a straight pulling force or slight twisting force. A breakaway position, as used herein, refers to a position in which the connectors can be separated with a straight or slight twisting force.

Threadably locked, as used herein, refers to a connection in which corresponding threads are engaged (e.g. screwed together) such that twisting force is necessary to unscrew or decouple the connectors.

Standard ISO-compliant connectors, as used herein, refer to small bore connectors for liquids and gases in healthcare applications that meet the standards for dimensions, rigidity, and other requirements as outlined in International Organization for Standardization (ISO) 80369 series of standards. These standardized connectors may be commercially available and in current use.

Selectable coupling or selectably coupled, as used herein, refers to the ability for the connector or coupler to be engaged with another connector in a first fitment position or a second fitment position, depending on a selection by a user according to preference or need.

Dimensionally compatible, as used herein, refers to features that have dimensions suitable for mating with a corresponding feature on another part, such as a nozzle and a receiver (i.e. cone and socket) in a friction fit or screw threads that couple together.

Male connectors or male coupler ends, as used herein, include an internal nozzle. Female connectors or female coupler ends, as used herein, include a receiver having an external wall that includes partial threads or is fully threaded.

Fluid, as used herein, refers to liquid or gas. The connectors are in fluid connection when coupled, such that fluid flows between the connectors without leaking.

Coupler, as used herein, refers to a part having opposed male and female connector ends that couple to external female connector and male connectors, respectively.

Tubing, as used herein, can refer to medical tubing or any device or vessel that could be understood by a person having ordinary skill in the art to be fitted with a small bore connector, such as syringes, stopcocks, bottle adaptors, needles, probes, containers, pouches, incorporated into tubing sets, and the like.

Opposing, as used herein, refers to paired features that are located opposite one another, For example, opposing threaded sections refer to a threaded section located 180 degrees (on center) on from another threaded section along the internal wall of the body. Opposing partial threads, or lugs, are paired and located 180 degrees (on center) from each other along the external wall of the receiver.

General Discussion

Presently, small-bore tubing connectors, or medical connectors, are used to connect tubing systems or syringes to tubes that deliver medications, therapies, and/or nutrition to patients or to withdraw gases (e.g. stomach gas) or fluids (e.g. blood, bile, cerebrospinal fluid) from the body.

Specific body systems or areas of therapy have dedicated connectors that are compatible with the International Organization for Standardization (ISO) 80369 series of small-bore tubing connector standards. For example, connectors for neuraxial applications comply with the dimensional specifications and criteria of the ISO 80369-6 standard, connectors for enteral applications comply with the dimensional specifications and criteria of the ISO 80369-3 standard, and intravascular/hypodermic/Luer connectors comply with the dimensional specifications and criteria of the ISO 80369-7 standard.

Some medical connectors that are presently in use couple together using threads such that the male and female connectors screw together. These are often referred to as locking connectors, such as a Luer lock. Alternatively, some medical connectors couple together in a friction (breakaway) fitment. There are presently no connectors or connector systems that allow a user to select either a threaded connection or breakaway connection within a single connector or coupler, depending on need. For example, there are times when the tubing can become entangled or snagged and the locking mechanism can cause the tubing to be pulled out of the patient's body. In these instances, a breakaway feature for the connectors is highly desirable as it could prevent patient harm and the need for additional medical interventions. There are particular use situations where snagging is more of a concern, like when an ambulatory patient is connected to long tubing lines during the administration of their medications or nutrition. There are also certain applications for which a locking connection of this same connector may be more preferable, such as when there is increased pressure when a syringe is connected to the patient's tube to provide a bolus of fluids. In other instances, clinicians, caregivers, and patients may have limited dexterity that can make it very difficult for them to screw and unscrew locking, threaded connectors. Additionally, some clinicians, caregivers, and patients may have a preference for a friction fit configuration. For these different use cases, environments, and user preferences, it is highly desirable for these tubing connectors to have the ability to either lock or to have a friction fitment that doesn't require screwing and can disconnect if the tubing is snagged. Of course, in allowing for these features, it is prudent to maintain compatibility with the standards of the ISO 80369 series to minimize the potential for cross-system tubing misconnections.

In accordance with the purpose(s) of the present disclosure, as embodied and broadly described herein, embodiments of the present disclosure, in some aspects, relate to small bore connectors for fluid transfer in medical applications.

In general, embodiments of the present disclosure provide for connectors and couplers for providing selectably locking coupling between a male and a female small bore connector.

An embodiment of the present disclosure includes a selectably locking coupler for providing selectably locking coupling between a male and a female small bore medical connector.

Another embodiment of the present disclosure includes a selectably locking male connector.

The present disclosure also provides for systems that include selectably locking male connectors and corresponding female connectors.

According to example embodiments, the male connector may incorporate opposing unthreaded sections that can be used to selectably configure its mating fitment to be either a threadably locking connection or a breakaway connection with a female connector that has opposing partial threads (also referred to as lugs). Unlike standard threaded connectors that have continuous threading, the selectably locking connectors include opposing threaded sections and opposing non-threaded sections. Medical couplings are typically made between a syringe, administration tubing, and the medical tubing that is connected to the patient or other medical application. Medical connectors for small bore connections are defined by the International Organization for Standardization (ISO) 80369 series of international standards. Within this series, a dedicated standard is provided for each bodily system so that its unique connectors are incompatible with the connectors that are dedicated to other bodily systems. This is done to minimize the chance of an inadvertent tubing misconnection between different bodily systems that could cause patient harm or death. To further minimize the chance for tubing misconnections, the couplings in the ISO 80369 series must all meet a material semi-rigidness requirement of >700 MPa because soft/flexible connectors are able to be force-fitted with things for which they are not intended, creating the possibility for medical tubing misconnections. It is a common feature of the couplings of the ISO 80369 series to have threaded connectors for a screwing fitment with their intended mating coupling. These screwing, also called locking, fitments can pose problems for those with limited dexterity and they can also increase the risks of tubing pull-outs. A tube pull out can happen when the tubing becomes snared or tangled on something and the line experiences tension. This tension or force pulls the line out of the patient because there is nowhere else for the force to go and there is nothing to break the force.

In example embodiments, the selectably locking connectors and couplers described herein provide for a selectable breakaway feature that can also be pressed together, instead of being screwed together. This allows the user, patient, clinician, or caregiver the ability to select a locking configuration using the same connectors. Furthermore, without fully disconnecting, the connectors can be switched back and forth between the locking and the breakaway configuration. The added safety benefits of the selectable breakaway feature and the added benefits to those who have dexterity issues should not cause incompatibility with the appropriate ISO 80369 series connectors nor compromise the minimized misconnection risks that are provided by the ISO 80369 series of standards. Thus, the selectably locking devices are compatible with dimensions of each applicable 80369 standard and meet other design criteria, like material hardness, provided in the standards.

Advantageously, the couplers and connectors described herein are dimensioned such that cross-connections between bodily systems cannot occur. For example, couplers or connectors dimensioned for enteral tubes will not allow for a connection between a male enteral tube and a female neuraxial tube.

Advantageously, the couplers provided herein allow for selectable coupling between a locking and a breakaway connection between existing equipment having ISO-compliant connectors. By using the couplers described herein, an end user can select a coupling setting between existing tubings or tubings and syringes that are fitted with standard connectors and are already in use. In this way, an end user can employ the selectable coupling with equipment from any manufacturer without the need for replacing the existing equipment.

Another advantage of the connectors and couplers provided herein is that a user (e.g. a patient or caregiver) can switch the connection between being in the locked position or the breakaway position, without having to disconnect or even break the seal of the connectors. In a non-limiting example, such a feature can be advantageous in a setting such as for a patient on a ten-hour continuous feed. The patient may want to have the connection in the locked position during sleep to prevent accidental disconnection in the middle of the night, but may want rotate to the breakaway configuration for the remaining waking hours of the feed so as to prevent a tube pullout or snag during more mobile periods of the feed. The two positions can be selected without disconnecting or interrupting the fluid delivery.

The couplers and connectors provided herein are compatible with ISO 80369 series and published subsections thereof that are current at the time of filing of the disclosure (e.g. 80369-1:2018, 80369-2:2024, 80369-3:2016, 80369-5: 2016, 80369-6:2016, 80369-7:2021, 80369-20:2015). However, ISO standards are typically reviewed every five years and subsequently may be updated and published as new editions. The dimensions of the couplers and connectors and/or particular features described herein can be updated for compatibility and/or compliance with the updated standards. Accordingly, reference to ISO-compliance or ISO-compatibility herein applies to both standards at the time of filing or future standards.

The connectors and couplers can be made of such as Acrylonitrile butadiene styrene (ABS), polyvinyl chloride (PVS), polyurethane, polypropylene, nylon, Tritan™, polycarbonate, high-density polyethylene (HDPE), or other suitable materials as would be understood by a person having ordinary skill in the art. The connectors and couplers can be manufactured using suitable means such as molding, milling, or additive printing.

The selectably locking connectors and couplers include threaded and unthreaded sections on an internal wall of the body. The threaded sections allow for the fully-threaded or partially-threaded female counterpart to be screwed into place on attachment and unscrewed on detachment. The unthreaded sections of the selectably locking connectors or couplers allow for its partially-threaded female counterpart to be engaged via a friction fitment that does not require a screwing action. The male connector's unthreaded sections also allow for its partially threaded female counterpart to be disengaged via a pulling force in the opposite direction of the male connector, which does not require an unscrewing action. This "breakaway" functionality helps to prevent patient harm if the patient's tubing becomes snagged. The clinician, caregiver, or patient can selectably engage the partially threaded female connector via either a screwing action or by aligning the female's opposing partial threads to the male's opposing unthreaded sections and pressing the two together. The clinician, caregiver, or patient can selectably disengage the partially threaded female connector via either an unscrewing action or by aligning the female's opposing partial threads to the male's opposing unthreaded sections and pulling the two apart. During engagement, the clinician, caregiver, or patient can select to have the partially threaded female connector threadably locked in place by engaging its opposing threads with the opposing threads of the male connector, or they can select to utilize the breakaway feature of the system by aligning the female's opposing partial threads with the opposing unthreaded sections of the male connector. Depending on the use environment, the particular application, or the user's preference, the clinician, caregiver, or patient can also select to use fully threaded female connectors that eliminate the slip fit and breakaway features previously described.

In example embodiments, the selectably lockable male connector or the selectably lockable coupler feature a "window" or "windows" along one or both of the opposing non-threaded sections. The circumferential length of a window is typically greater than or equal to the circumferential length of a corresponding partial thread, or lug, of a partially threaded female connector. The partial threads of the partially threaded female connector are positioned such that the partial threads are centered in the window when the connectors are coupled in the breakaway position. The window, or windows, provide for a visual indication of the alignment between the threaded and unthreaded sections of both connectors. This visual indication allows for the clinician, caregiver, or patient to see whether couplers are engaged in the threadably locked or breakaway position. In some embodiments, the window height is about equal to or slightly greater than the height of the lug so that the entire lug can be seen. Advantageously, the window, or windows, can also provide for improved flushing of the internal body and threads when the male connector or coupler is decoupled from its female counterpart.

In some embodiments, additional visual features can be included on the connectors or couplers to indicate the connection status (i.e. threadably locked position vs. breakaway position) of the coupling. For example, alignment arrows, grip tabs, wings, or wording can be included to communicate whether the coupling is in the threadably locked position or the breakaway position. For example, wings or tabs on the female connection may align with wings or tabs on the male coupler or connector to indicate that the connection is in the breakaway position. Alternatively, these features on the male coupler or connector may orient in an offset position to the features on the female connector to indicate that the connection is in the threadably locked position. In other embodiments, the female partial threads could be marked with such as "pull" or "unlocked", which can only be seen through the viewing window when in the breakaway position. In other embodiments, the partial threads of the female connector can have a different coloring or marking to help the user identify which position is selected. In yet other embodiments, a connector or coupler can be marked with arrows indicating which direction to twist the connection for a breakaway or locked position.

In some embodiments, the selectably locking connectors or couplers can include a cap or closure. In a particular embodiment, the nozzle end of the male connector or coupler can be capped by a female connector that lacks a through-bore. In other embodiments, a tethered plug that fits into the internal bore of the nozzle can be provided. The coupler or connector can include a channel for retaining the tether. Other caps or screw closures can be provided as would be understood by a person having ordinary skill in the art.

One problem with existing medical connectors is the risk of contamination that can result in infection. This can be exemplified with feeding tubes in clinical settings such as neonatal intensive care units (NICUs) where the risk of contamination is high and the consequences can be catastrophic, such as outbreaks of necrotizing enterocolitis (NEC). Advantageously, the selectably lockable couplers described herein can be temporarily affixed to tubings that are connected to the patient and the coupler can then be disposed of. In this way, the coupler acts prophylactically to the patient's tubing connector by preventing it from becoming soiled and/or contaminated because the interior surfaces of the tubing connector are blocked by the connection with the coupler and are not able to be contacted by fluids or debris. Medical tubings that are attached to patients should remain clean throughout the duration of use, which can last up to several months, depending on the particular tube. Tubings should not be changed out prematurely because this has associated risks of pain, discomfort, or even trauma. As a disposable prophylactic that blocks debris and contamination from contacting the patient's tubing connector, the tubing connector can remain clean and the use duration can be maximized, while the coupler is simply disposed of and replaced with a new coupler at some set interval or at the first signs of soiling. This prophylactic and proactive approach to preventing infections from contaminated tubing connectors is also highly desirable compared to the existing, reactive, processes that involve cleaning the tubing connectors with a brush, cleaning tool, foam swab, isopropyl alcohol wipe, or otherwise. The use of the coupler as a disposable guard against contamination is also preferred in that this process requires much less exertion than the reactive cleaning methods and the coupler, even as a disposable, can be significantly cheaper than the brushes and specialized tools that are used for reactive cleaning.

In some embodiments, the male and/or female connectors provided herein can be integral with medical tubing or integrally connected to a device or container (such as a syringe).

In example embodiments, the width of each of the male's opposing non-threaded, or unthreaded sections are typically greater than or equal to the width of the partial thread, or lug, of its corresponding partially threaded female connector (see dimension Y, FIGS. 10A, 12B, 15A).

In various embodiments, the male connector or the coupler includes tactile feedback features. These tactile features can include faint threads, a semiflexible leading edge, bowed geometry, or bumps. The tactile feedback features can be included alone or in combination to control the amount of separation force needed to disengage the connectors and to provide tactile feedback to a user.

In example embodiments, the tactile features are semiflexible sections along the leading edge or interior wall of the cylindrical surface of the male connector. These semiflexible sections, controlled through material thickness, material selection, the height and width of the aforementioned "window", and/or a bowed or elliptical shape of the cylindrical geometry, or other means, allows for a tactile snap when the connection is properly seated upon pressing together the connectors in the breakaway fitment with the opposing threads of the partially threaded female connector. Through design, these semi-flexible sections can be configured to provide more or less tactile feedback and greater or lesser connection forces and separation forces while having the flexure to still allow for the screwing and unscrewing of the connections when used in the selectably threaded configuration and or when used with a fully threaded female connector. The semiflexible section can be a minor lip on the interior wall in which the lip material is thinner than the crest of the threads but thicker than the root of the threads and thus aids in creating a tactile snap and controllable friction during connection and disconnection in the breakaway configuration In example embodiments, the tactile features are faint threads along the opposing unthreaded sections. These faint threads are a faint continuation of the male connector's threading that continues along the otherwise unthreaded opposing sections aforementioned. The faint threads typically have a depth of about 4% to about 40% of the thread depth in the threaded sections, or a thread depth of no more than about 60% of the thread depth in the threaded sections. The faint threads provide for a small bump that creates a tactile snap when the connection is properly seated upon pressing together the connectors in the breakaway fitment with the opposing threads of the partially threaded female connector. The continuation of the faint threads also allows for a smooth, or seamless, screwing and unscrewing action of the connections when used in the selectably threaded configuration and or when used with a fully threaded female connector. This faint continuation of the threading can be made larger or smaller and or its cross-sectional geometry can be altered to create more or less tactile feedback and more or less connection and separation forces. All of the aforementioned embodiments and features can be used independently or in combination to create and control the tactile snap and to control the amount of force needed for connection and separation, when used with breakaway fitment (straight press together or straight pull apart) configuration with the opposing threads of the partially threaded female connector.

Advantageously, the connectors and couplers provided herein engage and form a seal without the threaded components being fully tightened together. The connection's sealing surface is between the male nozzle and female receiver, forming a cone and socket seal even before the mating threads' engagement with one another is fully maximized. The length of engagement at which a seal is first formed between the nozzle and receiver is similar whether in a friction fit or a threadably locked connection. Enough sealing length, or distance between when a seal is made and when the connectors cannot be further tightened/screwed together, is available so that the selectably locking function allows the switch between the threadably locked and breakaway positions without breaking the seal. For example, from the breakaway position, the connection can be rotated a few degrees clockwise to tighten and the lug will engage the open space between threads to form a locked and slightly tighter seal. The user can then rotate in the opposite direction and return to the breakaway position. In example embodiments, the partially threaded female connector has opposing slots across the leading edge of its cylindrical surface. These slots allow for some flexure that aids the female connector in its ability to overcome the faintly threaded bump and other aforementioned features of the male connector that are meant to provide tactile feedback and to control connection and separation forces. The amount of flexure is controllable through the design, primarily the height, width, shape, and location of the slotted features.

In example embodiments, the selectably locking coupling and systems and methods disclosed herein are preferably usable and compatible with various types of syringes and connectors or couplings, for example, of the type formatted for intravenous/intravascular, enteral and neuraxial/neural applications. According to example embodiments, coupling and connectors such as those detailed in the ISO 80369 series of standards and are incorporated by reference herein and can be used with the selectably locking features of the present invention.

Also provided herein are methods for selectable coupling of fluid-delivery tubing. In one embodiment, the method can include connecting a selectably locking coupler to a male connector at a first end and a female connector at a second end. The male connector couples with the coupler only using a screwing action, so the breakaway connection occurs between the female connector and the coupler. A first position can be selected in which the connectors are threadably locked together by engaging the female connector's opposing partial threads with the opposing threaded sections of the male end of the coupler and by engaging the coupler's opposing partial threads at the female end with the opposing threaded sections of the male connector. The threadably locked coupling can be disengaged by unscrewing or by rotating the coupler into the second position. A second position can be selected in which the connectors are in a breakaway connection where the connectors can be engaged by a pushing straight force or disengaged by a pulling straight force. The second position can be selected by aligning the female connector's opposing partial threads to the selectably locking coupler's opposing unthreaded sections and pressing the coupler and female together. The connectors can be decoupled by pulling when the selectably locking coupler is coupled with the female connector in the second position. The coupler can be decoupled from one or both of the male or female connectors. The connectors can remain coupled and fluidly sealed and allow for continuous fluid communication therethrough when switching between the two connection types. In other words, the coupler need not be disconnected to change the selection between the breakaway or threadably locked connections.

The method can further include coupling the coupler with a connector attached to a patient's tubing to prophylactically prevent patient contamination. The coupler prevents or blocks debris and contamination from contacting the patient's tubing connector. The method can further include disconnecting the coupler from the patient's tubing connector and disposing of the coupler when soiled.

Also provided herein are methods for selectable coupling of fluid-delivery tubing. In one embodiment, the method can include connecting a selectably locking female connector to a male connector at a first end and a female connector at a second end. A first position can be selected in which the connectors are threadably locked together by engaging the female opposing partial threads with the male opposing threaded sections of the male connector or disengaged by unscrewing or by aligning the female's opposing partial threads with the opposing unthreaded sections of the male connector. A second position can be selected in which the connectors are in a breakaway connection where the connectors can be engaged by a pushing straight force or disengaged by a pulling straight force. The second position can be selected by aligning the female connector's opposing partial threads to the selectably locking male connector's opposing unthreaded sections and pressing the two connectors together. The connectors can be decoupled by aligning the female connector's partial opposing threads with the selectably locking connector's opposing unthreaded sections and pulling the two connectors apart.

The connectors can remain coupled and fluidly sealed, allowing continuous fluid communication therethrough when switching between the two connection types. In other words, the coupler need not be disconnected to change the selection between the breakaway or threadably locked connections.

The method can further include flushing the selectably locking male connector or coupler to remove debris or fluid from the connector or coupler body and/or threads. The flushing can be performed while the selectably locking male connector or coupler is capped, uncapped, or in a connected position with a female connector.

Having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Turning now to the drawings, exemplary embodiments are described in detail.

Example 1—Couplers

FIGS. 1A-1E provide an example of a coupler 1000 that enables standardized, ISO-compliant small-bore connectors to be selectably coupled in a first position or a second position. The first position is a locking configuration requiring screwing to couple or decouple; the second position is a breakaway configuration in which the components can be decoupled by application of a pulling force. The depicted embodiment shows the coupler 1000 coupling with ISO 80369-3 compliant or compatible connection features for enteral feeding systems, which are also referred to as ENFit™ connectors. However, as can be envisioned by a person having ordinary skill in the art, the dimensions of the coupler can be modified for compatibility with other ISO-compliant connectors including but not limited to intravascular connectors (e.g. ISO 80369-7 intravascular connectors), and neuraxial connectors (e.g. ISO 80369-6 connectors). FIG. 1A is a side view; FIG. 1B is a perspective view; FIG. 1C is a side view rotated 90 degrees from FIG. 1A; FIG. 1D is a top view from the male end; and FIG. 1E is a bottom view from the female end.

Coupler 1000 has a body 1100 connecting a male end 1200 with a female end 1300, where the male end 1200 and a female end 1300 are on opposing ends of the body 1100. The male end 1200 is formed from a nozzle with a tapered end 1210 that are dimensionally compatible for coupling with a corresponding female ISO-connector. The female end 1300 includes partial threads 1310 (also referred to as lugs) that are dimensionally compatible for coupling with a corresponding standard male ISO-connector. The internal surface of the body 1100 has opposing threaded sections 1130. The opposing threaded sections 1130 alternate with opposing unthreaded sections 1140. Each of the opposing unthreaded sections 1140 typically has a width greater than or equal to the width of the partial thread, or lug, of its corresponding partially threaded ISO compliant or compatible female connector (see dimension Y, FIGS. 10A, 12B, 15A)

A lumen or central bore 1400 runs through the nozzle along the axis of coupler 1000, such that when the coupler 1000 is coupled with a male and a female standard ISO connector, the central bore 1400 allows for fluid flow through the coupler 1000. The wall of the body 1100 can include a cutout or window 1120 positioned in place of an unthreaded section 1140. The body can also include opposing wings 1110 that provide an extra gripping surface to allow a user to rotate the coupler during screwing, unscrewing, or rotation between the first and second positions. Although not shown, other gripping features such as knurls can be substituted for the wings 1110.

In some embodiments, the unthreaded sections 1140 can be faintly threaded, where the thread depth is less than that of the threaded sections 1130 but form a continuation of the threaded sections' 1130 threading. This faint threading can provide tactile feedback to the user and increase the amount of force that is needed to separate the connectors in the second, breakaway position.

In some embodiments (not shown), the female end 1300 can include full threads instead of partial threads 1310.

Figures 2A, 2B, 2C:
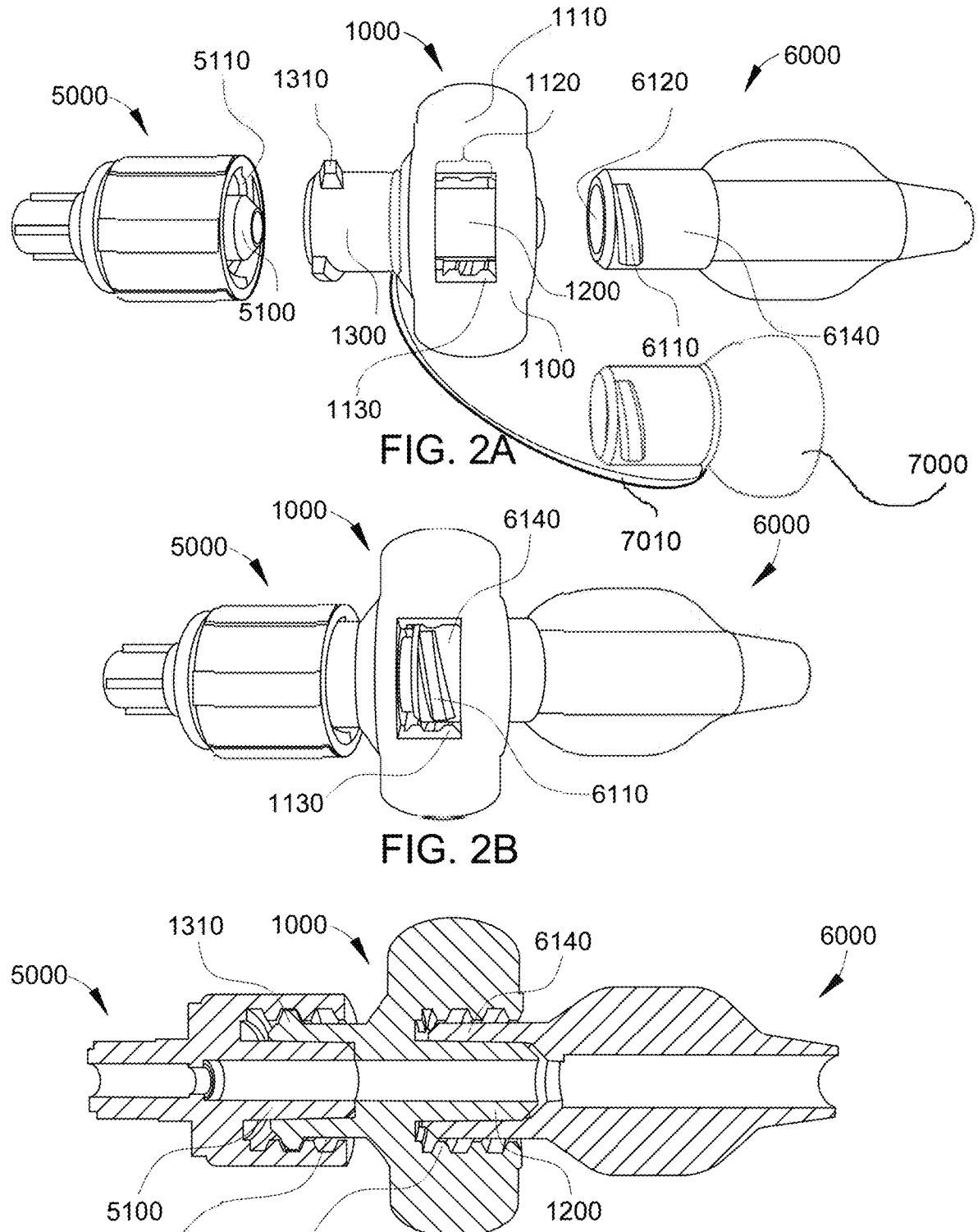
FIGS. 2A-2F are drawings of a coupler in various stages of connection with a male and female ISO compatible connectors according to various example embodiments.

FIGS. 2A-2F are drawings of the coupler 1000 of FIGS. 1A-1E in various stages of connection with a standard male ISO-compliant connector 5000 and standard, partially-threaded female ISO-compliant connector 6000. For illustration purposes, the tubing to which connectors 5000 and 6000 are attached is not shown. FIG. 2A shows the coupler 1000 and the connectors 5000 and 6000 in an exploded view with connectors 1000 and 6000 orientated for a breakaway connection. Standard male ISO-compliant connector 5000 includes a nozzle 5100 and male threads 5110 on the internal surface of its body. The female end 1300 receives the nozzle 5100 and the female partial threads 1310 are dimensioned to engage with the male threads 5110. The standard female connector 6000 includes a female receiver 6120 in the female nozzle 6140, where the female receiver 6120 receives the nozzle of the male end 1200 and threaded sections 1130 are dimensioned to selectably engage with the partial threads 6110. In alternative embodiments, in place of partial threads 1310, the female end 1300 can be fully threaded to engage with the male threads 5110.

FIG. 2B shows the coupler 1000 and the connectors 5000, 6000 all coupled together with connectors 1000 and 6000 orientated in a breakaway position, also referred to as a second position, in which the standard female connector 6000 can be decoupled from the coupler 1000 by a pulling force or coupled by a pushing force, where the coupling is maintained by a friction fit. In the second position, as can be seen in the figure, the coupler 1000 and female connector 6000 are rotated relative to one another such that the partial threads 6110 are aligned with the unthreaded sections 1140. Because the partial threads 6110 do not have corresponding threads to mate with in the unthreaded sections 1140, the two components may be separated by pulling them apart. The force necessary to pull the components apart may be increased by the presence of faint threads on unthreaded sections 1140. The partial threads 6110 are viewable through window 1120, providing a visual indicator to the user that the coupler 1000 is in a breakaway coupling position. FIG. 2C is a cross-sectional view of FIG. 2B, in which the nozzle of the male end 1200 is inserted in the female nozzle 6140, and partial threads 1310 are engaged with the male threads 5110. As can be seen, partial threads 6110 are not engaged with threaded sections 1130, thus the female connector 6000 can be decoupled from coupler 1000 with a pulling force.

Figures 2D, 2E, 2F:
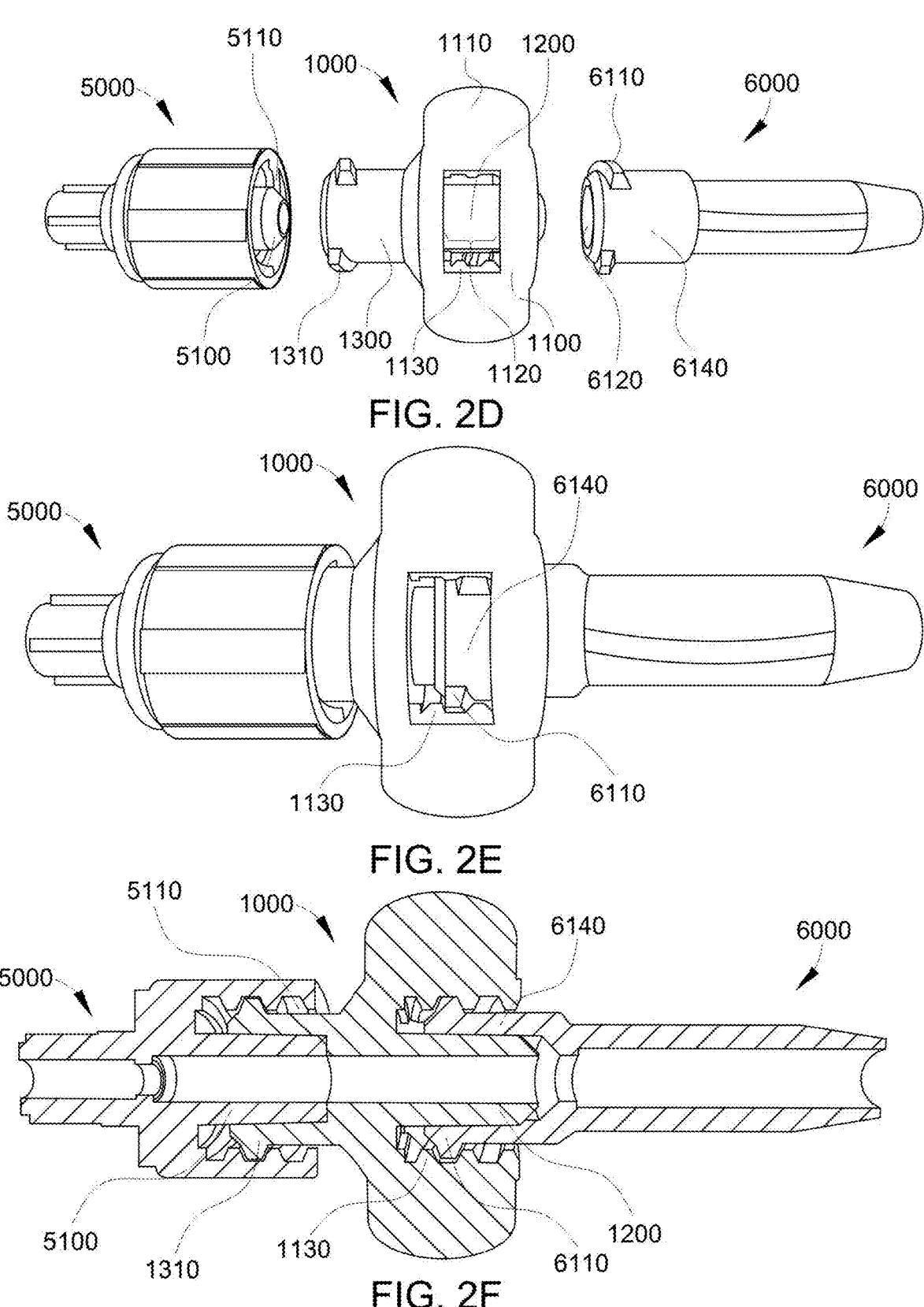

FIG. 2D shows an exploded view of the same components shown in FIG. 2A, however the female connector 6000 is rotated such that partial threads 6110 are in a position to engage with threaded sections 1130 such that the coupler and the connectors couple in a threadably locked connected position, also referred to as a first position. FIG. 2E shows the 1000 and the connectors 5000, 6000 in a threadably locked connected position. In the first position, as can be seen in the figure, the coupler 1000 and female connector 6000 are rotated relative to one another such that the partial threads 6110 are threadably connected to the threaded sections 1130. The partial threads 6110 are not fully viewable through windows 1120, their absence providing a visual indicator to the user that the coupler 1000 is in the threadably locked coupling position. FIG. 2F is a cross-sectional view of FIG. 2D. As can be seen, partial threads 6110 are threadably engaged with threaded sections 1130, thus the female connector 6000 cannot be decoupled from coupler 1000 with pulling force and instead the components would be unscrewed in order to decouple.

Example 2—Connectors

Figures 3A, 3B:
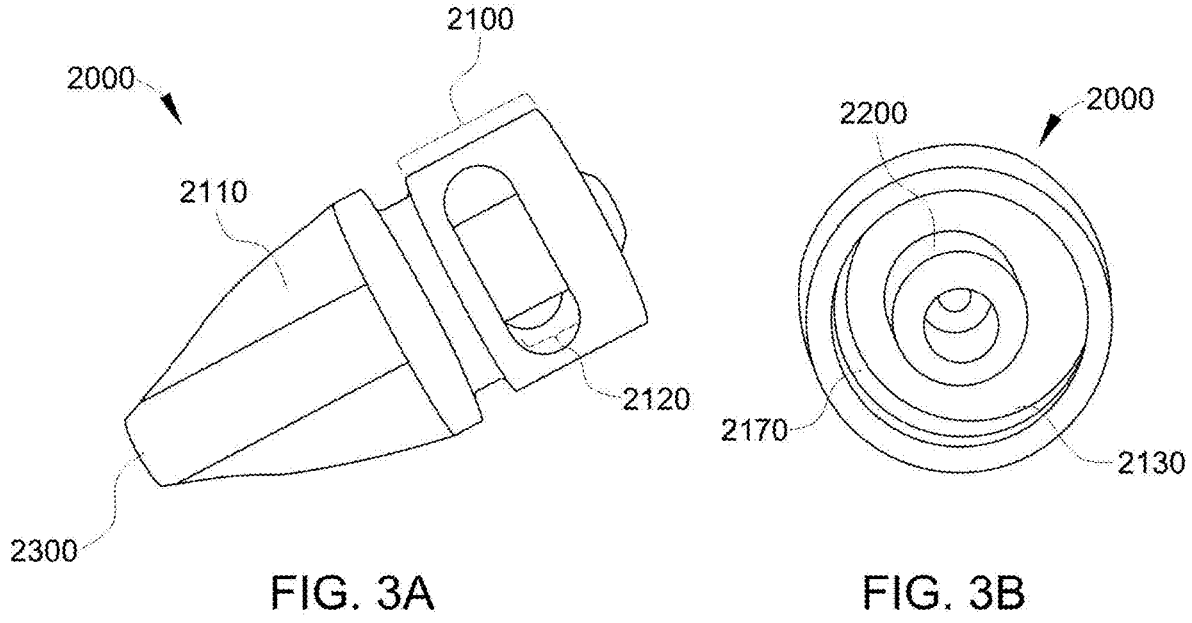
FIGS. 3A-3D are drawings of a male connector according to various example embodiments.

FIGS. 3A-3D are an example of a selectably locking male connector 2000. FIG. 3A shows a side perspective view of male connector 2000 having cylindrical body 2100 at the proximal end for receiving a female connector. Connection end 2300 can be integrally or permanently connected to tubing or a syringe barrel. The depicted embodiment shows wings 2110 to facilitate gripping and turning. Window 2120 is a cutout through the wall of the cylindrical body 2100, through which nozzle 2200 can be seen. The nozzle 2200 comprises a tapered end 2210. FIG. 3B shows a view from the proximal end of cylindrical body 2100 in which the nozzle 2200 and internal bore 2400 are shown.

Figures 3C, 3D:
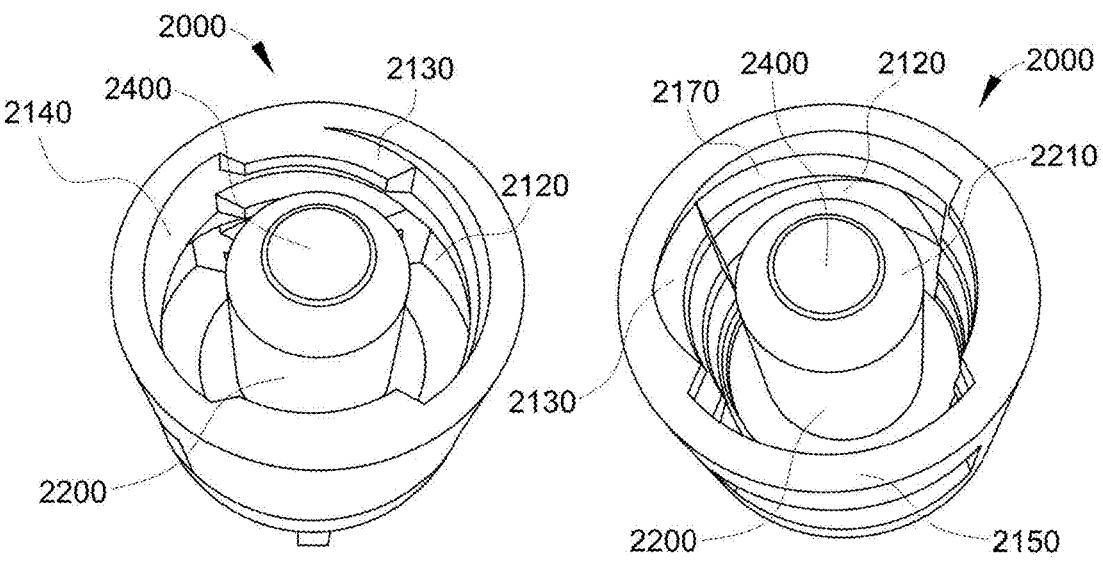

FIG. 3C shows a perspective view of the male connector's nozzle end. The internal wall of cylindrical body 2100 includes opposing threaded sections 2130, between which is an unthreaded section 2140 and window 2120 on the left side of figure and a faintly threaded section 2170 and window 2120 on the other side (right). This figure is intended to depict two alternative possible options; the connector can have two unthreaded sections, two lightly threaded sections, or have one of each. FIG. 3D shows a variation of the male connector 2000 from FIG. 3C that has been rotated 90 degrees. In this embodiment, opposing threaded sections 2130 are separated by faintly threaded sections 2170, where faintly threaded sections 2170 form a continuation of the normally threaded sections' 2130 threading. These faintly threaded sections 2170 allow for a slight engagement with the opposing threads of the partially threaded female connector so that a tactile snap is felt when pressing the connectors together or when pulling the connectors apart. The size and cross-sectional geometry of this faint continuation of the threading can be adjusted to produce more or less tactile feedback and require more or less connection and separation force. Window 2120 is shown at the bottom of the figure. In this figure, cylindrical body 2100 includes opposing semiflexible surfaces 2150 that feature a minor lip on the interior side, in which the lip material is thinner than the crest of the threads but thicker than the root of the threads and thus aid in creating a tactile snap and controllable friction during connection and disconnection in the breakaway configuration.

Figures 4A, 4B:
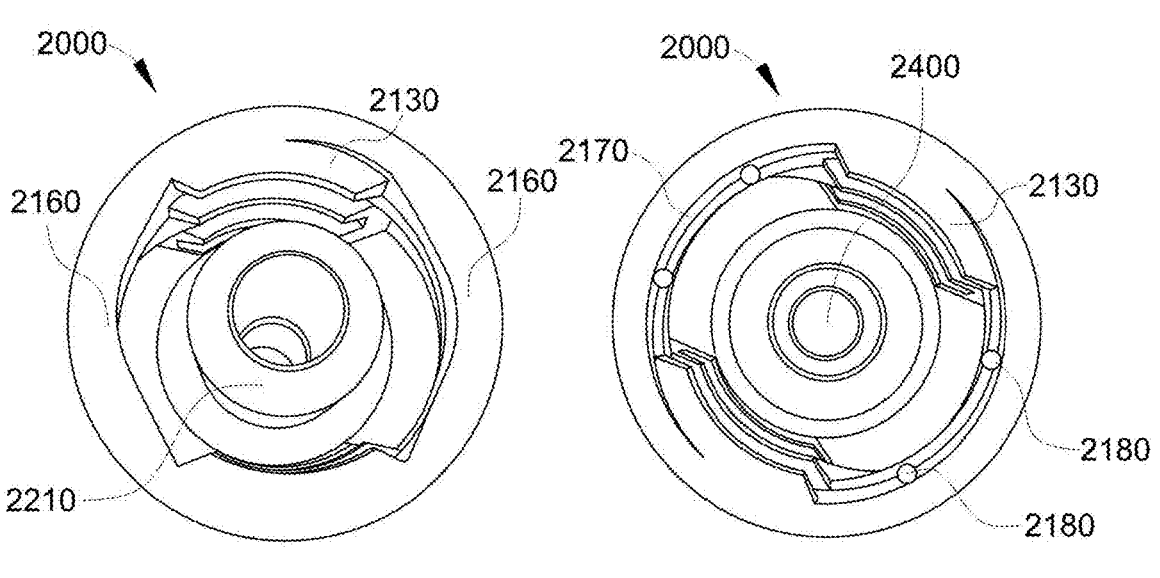
FIGS. 4A-4D are drawings of a male connector according to other various example embodiments.

FIG. 4A shows another embodiment of a male connector 2000 from a perspective view of the proximal end, in which opposing unthreaded sections 2140 feature a semiflexible bowed or elliptical geometry 2160 along the internal wall instead of the normally circular surface. This semiflexible bowed or elliptical geometry 2160 allows for a slight engagement with the corresponding threads of a partially threaded female connector (not shown) so that a tactile snap is felt when pressing the connectors together or when pulling the connectors apart. This bowed or elliptical geometry 2160 can be adjusted to produce more or less tactile feedback and require more or less connection and separation force.

FIG. 4B shows another embodiment of the male connector, wherein opposing faintly threaded sections 2170 feature bumps 2180 along the upper edge of the interior cylindrical geometry of the body 2100. These bumps 2180 or similar projections allow for a slight engagement with the opposing threads of the partially threaded female connector so that a tactile snap is felt when pressing the connectors together or when pulling the connectors apart. In another embodiment (not shown), the wall thickness of cylindrical body 2100 can be controlled to allow for a slight engagement with the opposing threads of the partially threaded female connector so that a tactile snap is felt when pressing the connectors together or when pulling the connectors apart. The thickness can be adjusted along the opposing unthreaded sections 2140 or faintly threaded sections 2170. This thickness can be adjusted to produce more or less tactile feedback and more or less connection and separation forces.

Figures 4C, 4D:
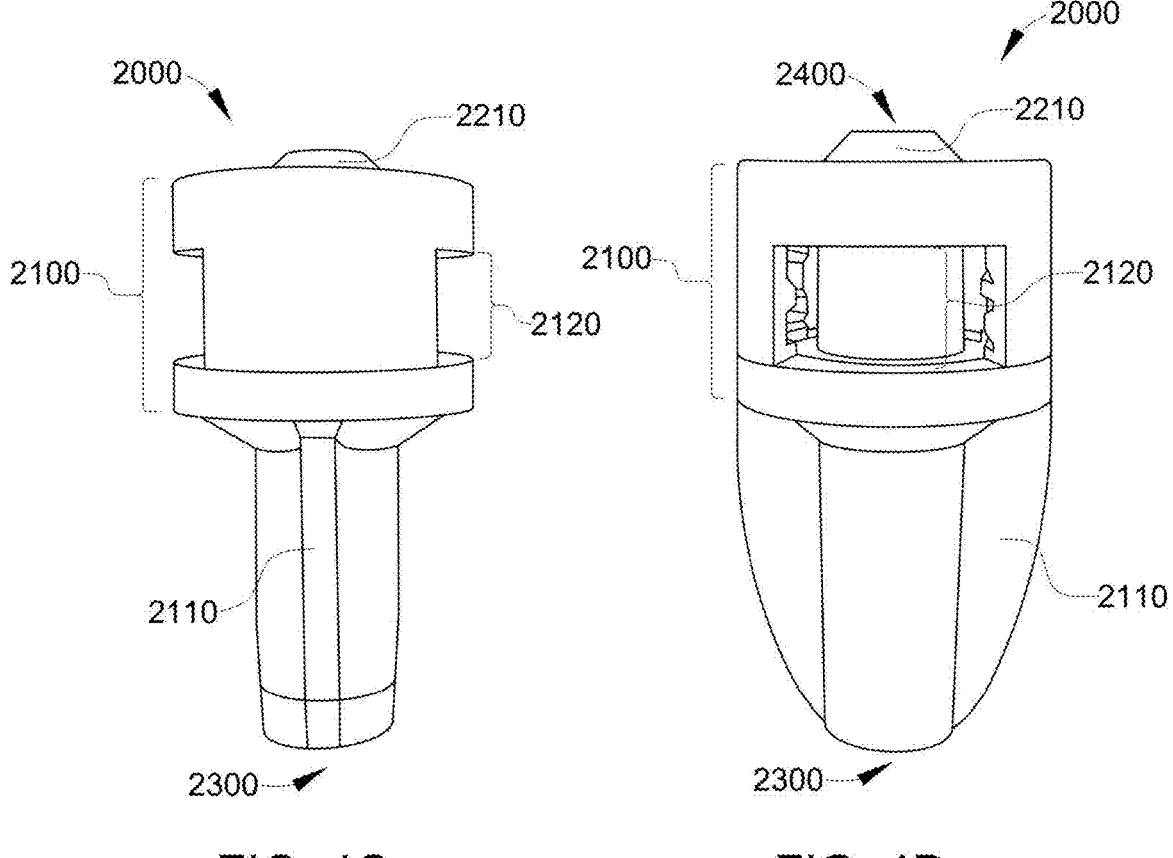

FIG. 4C shows a side view of another example embodiment of the male connector 2000, in which two opposing windows 2120 are present. Each window 2120 is located between the opposing threaded sections 2130. The height and width of windows 2120 can be controlled independently or in combination with the aforementioned tactile features to allow for a slight engagement with the opposing partial threads (lugs) of a corresponding partially-threaded female connector so that a tactile snap is felt when pressing the connectors together or when pulling the connectors apart. FIG. 4D shows a side view of the connector 2000 shown in FIG. 4C, rotated 90 degrees such that the opposing widows 2120 are aligned and the nozzle 2200 is visible through the windows 2120. The opposing threaded sections 2130 are on the left and right sides of the figure and are visible through the windows 2120.

FIGS. 5A-5E show a side view of the engagement of a male connector 2000 according to the present disclosure with a standard female ISO-compliant connector 3000. The female connector shown is an ISO 80369-3 compliant connector for enteral feeding systems (e.g. ENFit™ connector). The depicted male connector 2000 is dimensioned to couple with the ISO 80369-3 female connector 3000. However, as can be envisioned by a person having ordinary skill in the art, the dimensions of the male connector 2000 can be modified for compatibility with other ISO-compliant female connectors including but not limited to intravascular connectors (e.g. ISO 80369-7 connectors), and neuraxial connectors (e.g. ISO 80369-6 connectors).

Figures 5A, 5B, 5C:
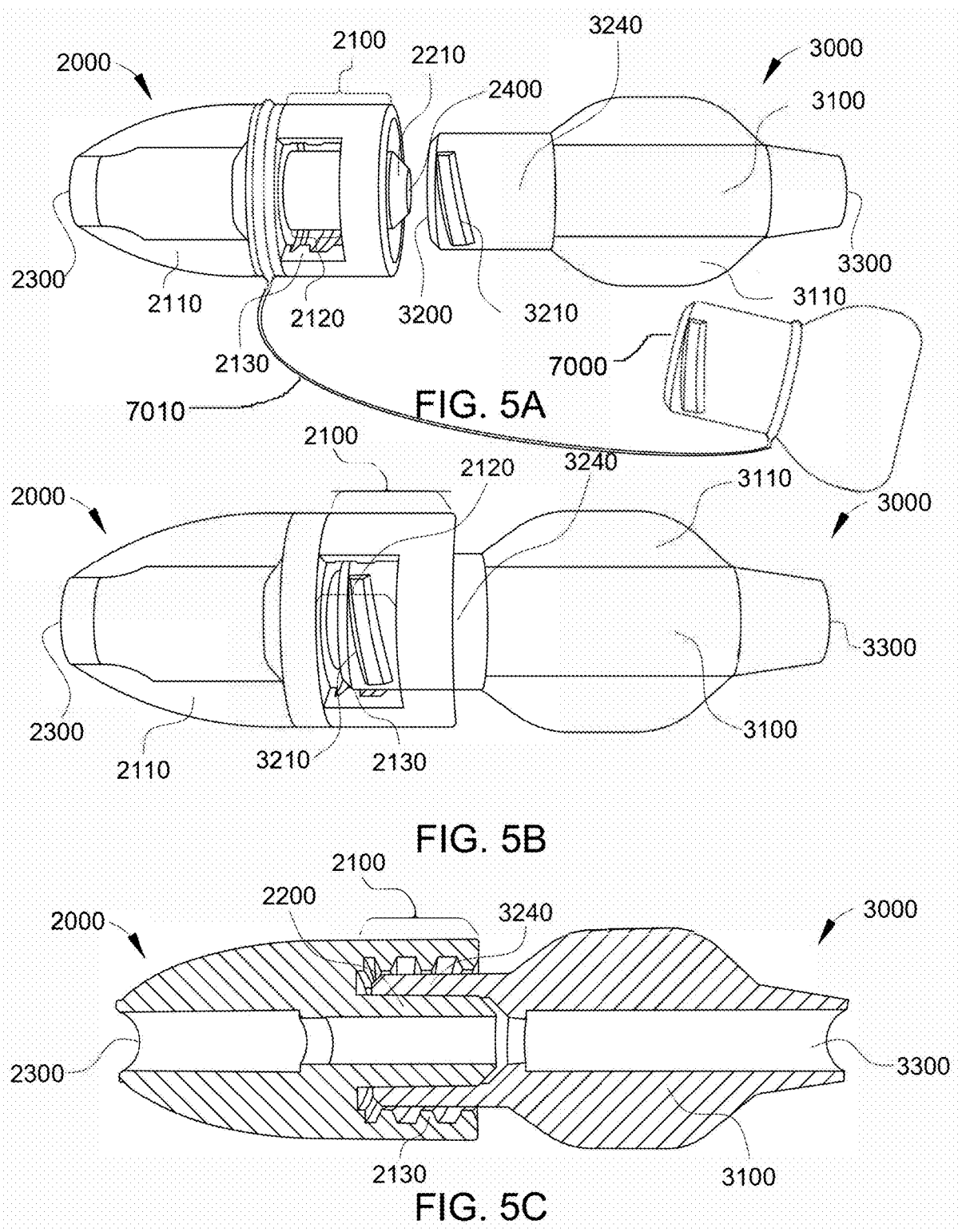
FIGS. 5A-5E are drawings showing the engagement of a female and a male connector according to various example embodiments.

FIG. 5A shows male connector 2000 and partially threaded female connector 3000 separate from one another and orientated for a breakaway connection configuration. FIG. 5B shows the connectors 2000 and 3000 in a breakaway connected position, also referred to as a second position, in which the standard female connector 3000 can be decoupled from the male connector 2000 by a pulling force or coupled by a pushing force, where the coupling is maintained by a friction fit. In this second position, as can be seen in the figure, the male connector 2000 and female connector 3000 are rotated relative to one another such that the partial threads 3210 are aligned with the unthreaded windows 2120. This connection configuration is indicated to the user by the visibility of the partial threads 3210 (also referred to as lugs) of the female connector being centered in the opposing threadless windows 2120 of the male connector. Because the partial threads 3210 are not screwed into the threaded sections 2130, the two components may be separated by pulling them apart and coupled by a straight force pushing the two connectors together. This breakaway connection configuration can also be separated by rotating the two connectors counterclockwise from a second position until the opposing partial threads 3210 of the female connector mate with the threaded sections 2130 and the connectors can then be unscrewed. FIG. 5C is a cross-sectional view of the fitted connectors in FIG. 5B in which the nozzle 2200 is inserted in the female receiving nozzle 3200 but female partial threads 3210 are not threadably connected with the male threaded sections 2130. In this second position, the interior wall of female nozzle 3240 is engaged in a friction fit against the outer surface of male nozzle 2200, such that the two connectors are snugly sealed together without being threaded. Although an embodiment having windows is shown in FIGS. 5A-5F, the windows can be omitted such that an unthreaded section 2140 or faintly threaded section 2170 exists in place of the windows. Such a configuration allows for a selectable breakaway or threadably locking configuration without the visual indicator. Alignment arrows, tabs, wings, or other visual indicators of the position could be substituted for the windows in some embodiments.

Figure 5D:
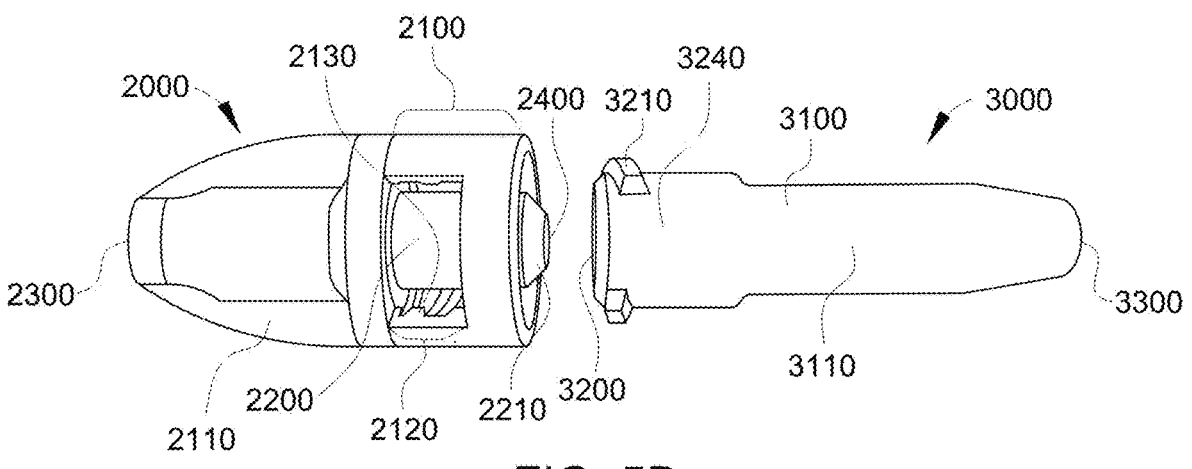
Figure 5E:
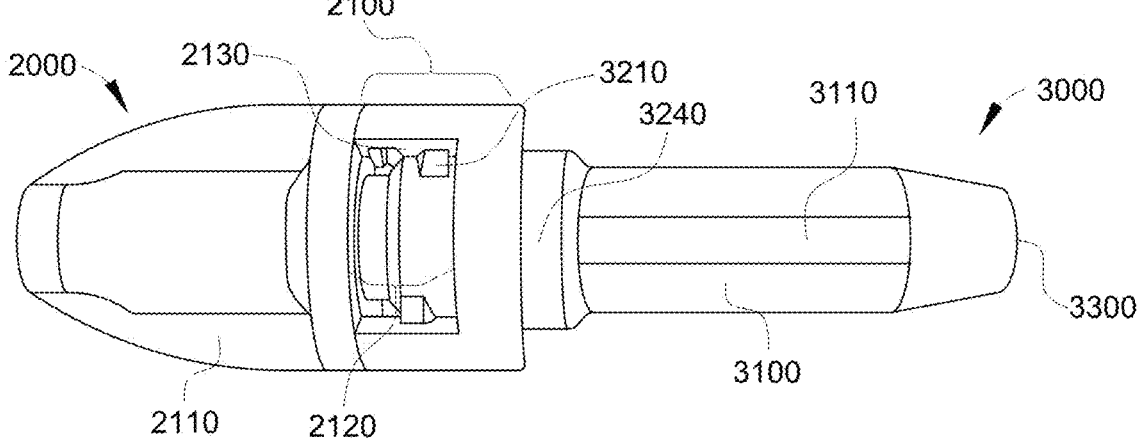
Figure 5F:
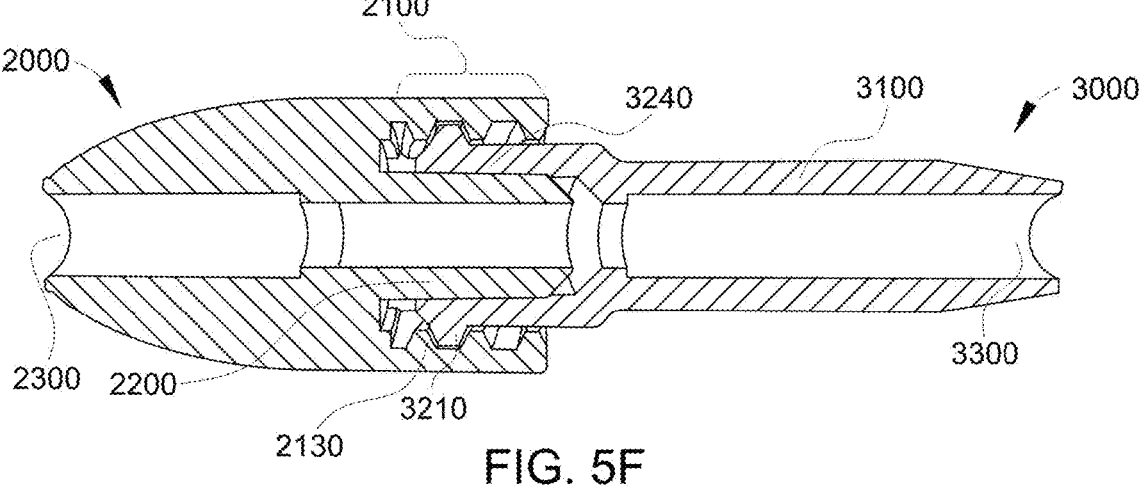
FIG. 5F is a cross-sectional view of the fitted connectors in FIG. 5E.

FIG. 5D shows the same connectors as in FIG. 5A, however the female connector 3000 is rotated such that partial threads 3210 are positioned to engage with threaded sections 2130 such that the coupler and the connectors couple in a threadably locked connected position, also referred to as a first position, where the female connector is in a threaded, or locking, fitment with the male connector. FIG. 5E shows the connectors 2000 and 3000 in threadably locked position, also referred to as a first position. Connectors 2000 and 3000 can be coupled in the first position by screwing the two connectors together and decoupled by unscrewing. First position coupling can also be separated by unscrewing the two connectors until they are in the breakaway configuration shown in FIG. 5B and then a straight, pulling force can be used to pull the connectors apart. First position coupling can also be achieved by pressing connectors 2000 and 3000 together with a straight force initially then rotating to cause the threads 3210 to engage in the locking configuration. The user can visually detect first position coupling in which breakaway coupling is disabled by viewing the uncentered alignment of the partial threads 3210 of the female connector in the window(s) 2120 of the male connector. FIG. 5F is a cross-sectional view of the fitted connectors in FIG. 5E. As can be seen, nozzle 2200 is inserted in female receiver 3200 and partial threads 3210 are threadably engaged with threaded sections 2130, thus the female connector 3000 cannot be decoupled from connector 2000 with pulling force and instead the components are coupled and decoupled by screwing or unscrewing.

Figures 6A, 6B:
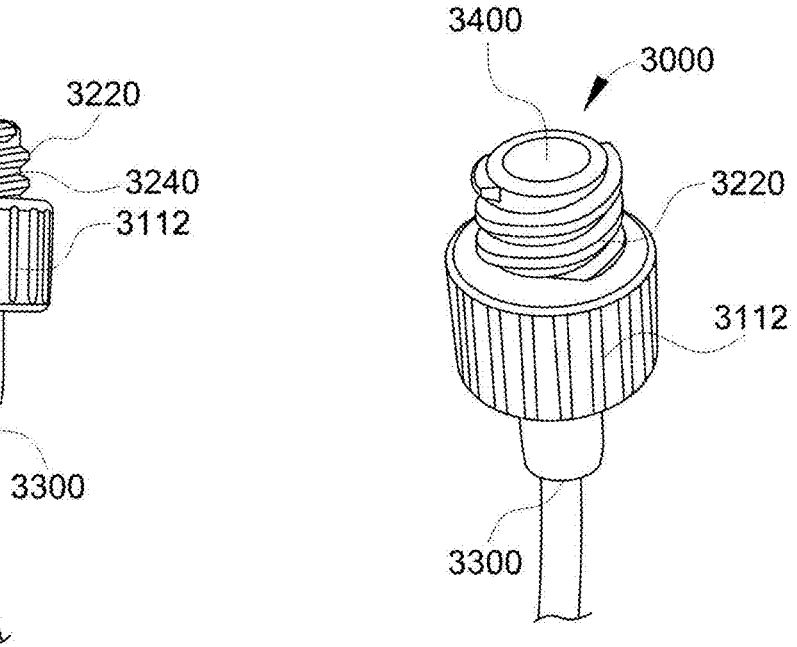
FIGS. 6A and 6B are drawings showing a fully threaded female connector according to various example embodiments.

FIGS. 6A and 6B are examples of a standard fully threaded female ISO 80369-3 connector 3000, shown in a side view and perspective view, respectively and connected to tubing at tubing end 3300. This connector is provided to illustrate one type of fully threaded connectors that are compatible with the selectably locking male connectors provided herein. In place of the previously described partial threads 3210, the female receiver has full threads 3220 on the external wall of female nozzle 3240. Internal bore 3400 allows fluids to pass through female connector 3000 from the tubing. Fully threaded female connectors allow for the breakaway feature of the selectably locking male connector to be disabled. In this way, tubing having a selectably locking male connector can be connected to a patient, but the ability to use the breakaway feature can be disabled when a breakaway option is not desired without the need for removing the tubing from the patient. In the depicted embodiment, the body includes knurls 3112 to provide for gripping. As can be envisioned by a person having ordinary skill in the art, the dimensions of the connector 3000 can be modified for compatibility with such as ISO 80369-6 or ISO 80369-7 male connectors as described herein.

Figures 7A, 7B:
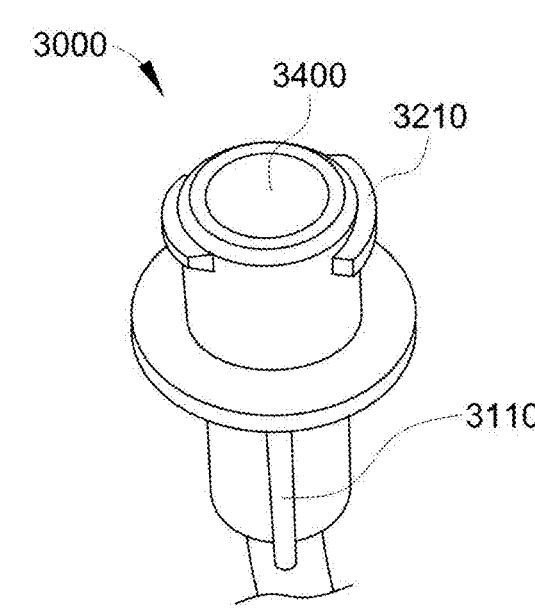
FIGS. 7A and 7B are drawings showing a partially threaded female connector according to various example embodiments.

FIGS. 7A and 7B are views of another example of a standard partially threaded female ISO 80369-3 connector 3000, shown in a side view and perspective view, respectively and connected to tubing at tubing end 3300. This connector is provided to illustrate one type of partially threaded connectors that are compatible with the selectably locking male connectors provided herein. Connector 3000 has opposing partial threads 3210 that engage with the internal male threaded sections 2130 or 1130 of the selectably locking male connector 2000 as described above. A ring to assist in pulling force can be included between the base of the female receiver 3200 and cylindrical body 3100. Female connectors 3000 with opposing partial threads 3210 allow for the clinician, caregiver, or patient to be able to select either a locking or a break-way connection with the selectably locking male connectors described herein. A nozzle 2200 of a selectably locking male connector 2000, as described herein, inserts into internal bore 3400 and allows fluids to pass from the tubing through female connector 3000 to the patient. As can be envisioned by a person having ordinary skill in the art, the dimensions of the connector 3000 can be modified for compatibility with such as ISO 80369-6 or ISO 80369-7 male connectors as described herein.

Figures 8A, 8B:
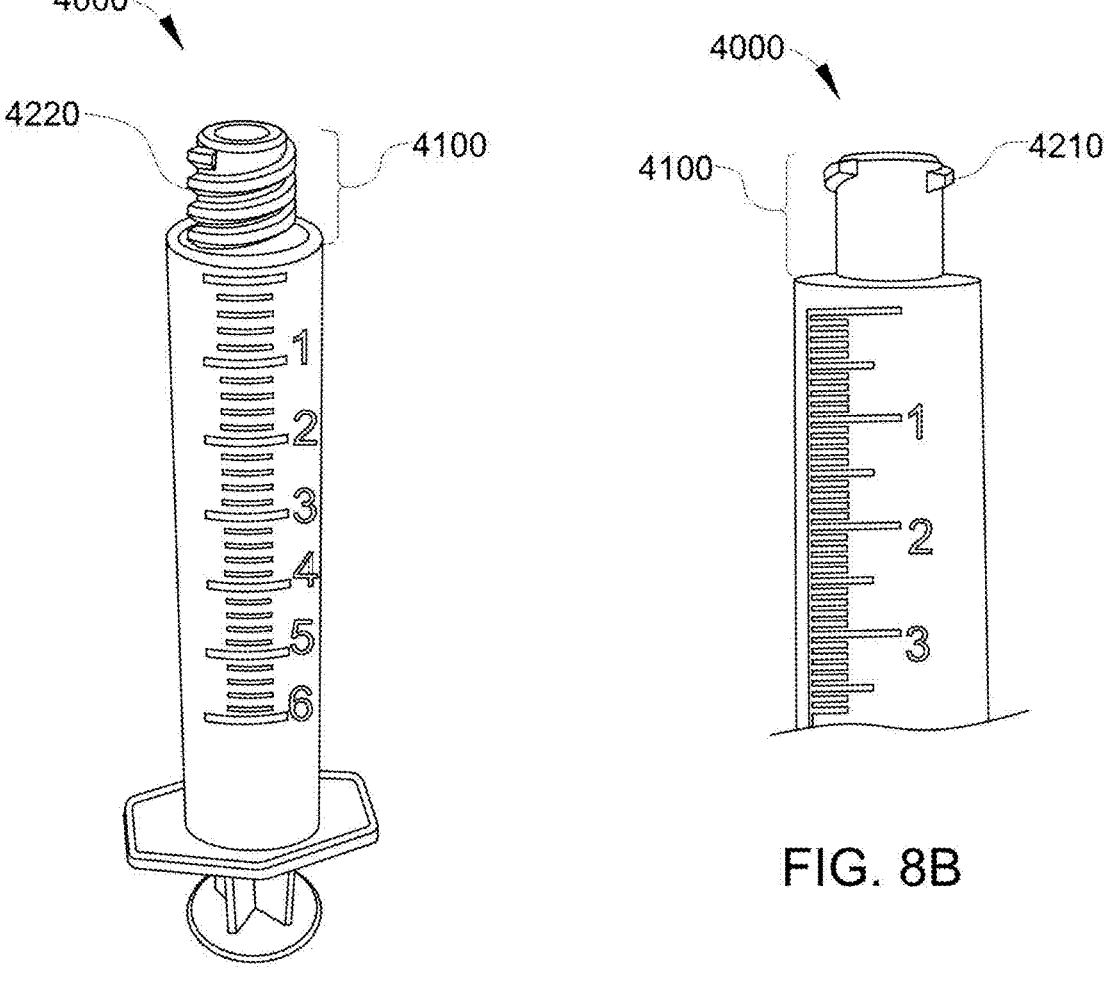
FIG. 8A shows a perspective view of a fully threaded female connector on the end of a syringe, according to a known embodiment.
FIG. 8B shows a side view of a partially threaded female connector, according to an example embodiment.

FIG. 8A shows a first perspective view of a standard, ISO 80369-3 syringe 4000 (commonly referred to as an ENFit™ syringe) having an integral female connector at the tip. Connector body 4100 includes full threads 4220. Fully threaded female connectors allow for the breakaway feature of the male connector 2000 to be disabled. In this way, tubing having a selectably locking male connector can remain connected to a patient, but if the breakaway option is not desired, a fully threaded syringe 4000 can be connected or disconnected only by screwing or unscrewing the syringe 4000 from the selectably locking male connector 2000. FIGS. 8A and 8B are provided to illustrate other types of female connectors that are compatible with the selectably locking male connectors provided herein.

FIG. 8B shows a side view of a standard, partially threaded female ISO 80369-3 syringe 4000 (commonly referred to as an ENFit™ syringe) having an integral female connector at the tip. Opposing partial threads 4210 allow for the clinician, caregiver, or patient to be able to select either a locking or a break-way connection with a selectably locking male connector 2000 as described herein. Partially threaded female syringe 4000 can be coupled with selectably locking male connector 2000 in the first, or threadably locked, position by screwing the two connectors together and decoupled by unscrewing. First position coupling can also be separated by unscrewing the two connectors until they are in the breakaway configuration and then a straight, pulling force can be used to pull the connectors apart. First position coupling can also be achieved by syringe 4000 and selectably locking male connector 2000 together with a straight force initially then rotating to cause the partial threads 4210 to engage in the threadably locked configuration. The user can visually detect first position coupling in which breakaway coupling is disabled by viewing the uncentered alignment of the partial threads 4210 of the female connector in the window(s) 2120 of the male connector or use of other visual indicators as provided herein.

Partially threaded female syringe 4000 can be coupled with selectably locking male connector 2000 in a breakaway connected position, also referred to as a second position, in which the syringe 4000 can be decoupled from the male connector 2000 by a pulling force or coupled by a pushing force, where the coupling is maintained by a friction fit. In this second position, as can be seen in the figure, the male connector 2000 and syringe 4000 are rotated relative to one another such that the partial threads 4210 are aligned with the unthreaded windows 2120. This connection configuration is indicated to the user by the visibility of the partial threads 4210 of the female connector being centered in the opposing threadless windows 2120 of the male connector. Because the partial threads 4210 are not screwed into the threaded sections 2130, the two components may be separated by pulling them apart and coupled by a straight pushing the two connectors together.

Figures 9A, 9B, 9C, 9D:
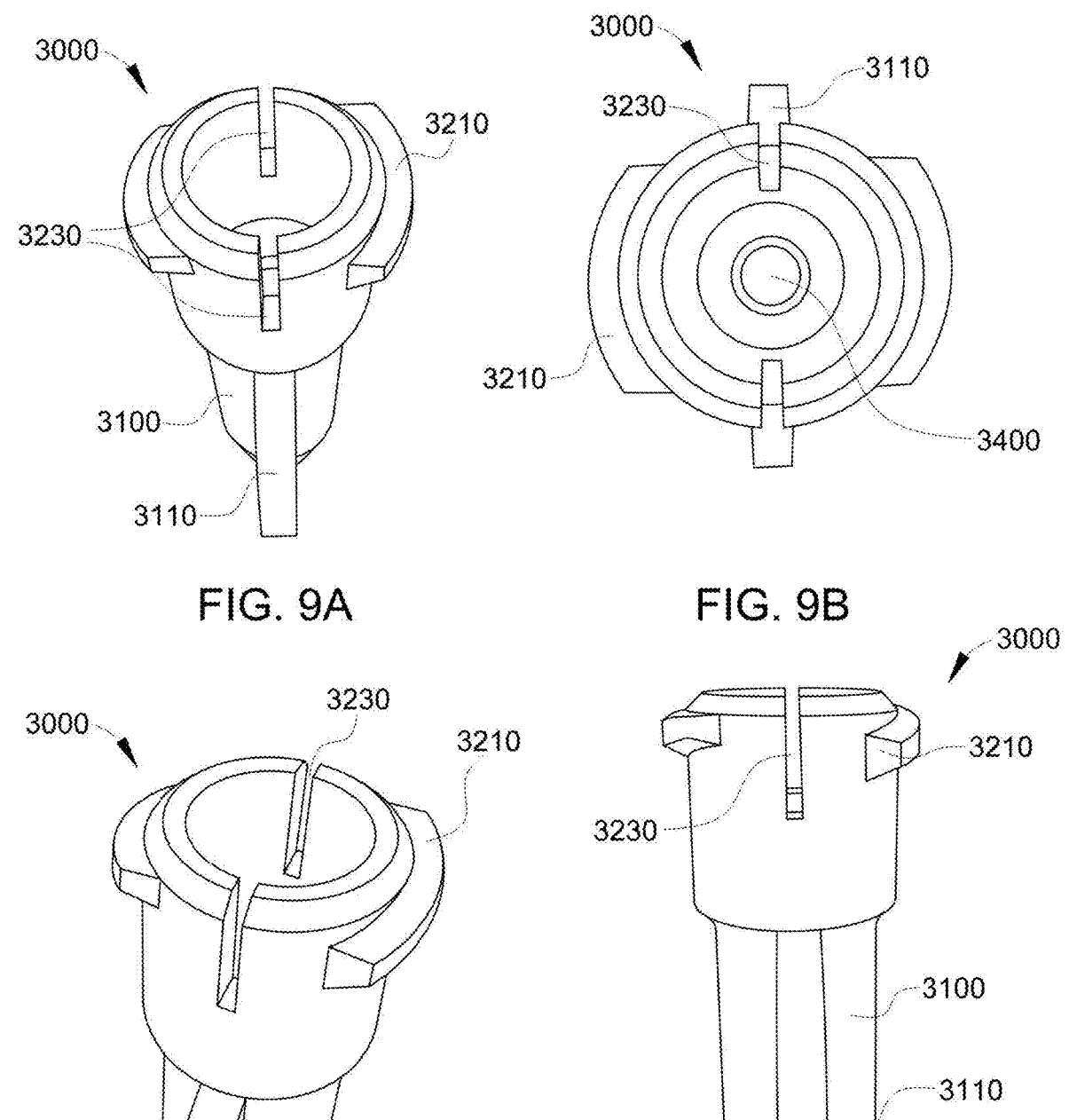
FIGS. 9A-9B are drawings of a partially threaded female connector having opposing slots to allow for inward flexure of the partially threaded sections, according to various example embodiments.
FIG. 9C is a second perspective view.
FIG. 9D is a side view.

FIG. 9A shows a first perspective view of a partially threaded female ISO 80369-3 compatible female connector 3000. Opposing slots 3230 allow for inward flexure of the body 3200 sections that include partial threads 3210, providing an easier fitment with the features of the male connector 2000's opposing unthreaded sections 2140. The height, width, shape and other aspects of the slots 3230 can be adjusted to control the amount of connection force, separation force, and the level of tactile feedback and clicking sensation that occurs on connection and disconnection between the opposing unthreaded sections 2140 of the male connector 2000 and the opposing partial threads 3210 of the partially threaded female connector 3000. FIG. 9B shows an overhead view of the female connector 3000 with slotted features shown in FIG. 9A. FIG. 9C shows another perspective view of the female connector 3000 with slotted features shown in FIG. 9A. FIG. 9D shows a side view of the female connector 3000 with slotted features shown in FIG. 9A.

FIGS. 10A-10C are standard female ISO 80369-6 neuraxial connectors 3000, which are also referred to as NRFit™ connectors. FIGS. 10A and 10B are a partially threaded version, as described with reference to FIGS. 7A and 7B, and are dimensioned for compliance with ISO 80369-6:2016 standards for misconnection mitigation; FIG. 10C is a fully threaded version, as described with reference to FIGS. 6A and 6B, and is dimensioned for compliance with ISO 80369-6:2016 standards for misconnection mitigation. The dimensions shown in Table 1 represent the dimensions specified in the most current version of ISO 80369-6 and are for reference only. Table 1 values expressed as a dash, "-", represent boundless values.

TABLE 1

Dimensions of a standard ISO 80369-6 Female Neuraxial Connector.
ISO 80369-6 Female Neuraxial Connector with Lugs

| | | Dimensions (mm) | | |
|---|---|---|---|---|
| Reference | Designation | Minimal | Nominal | Maximum |
| (A) | Angle of taper (5% taper nominal) | — | (2.86°) | — |
| B | Angle of the external thread profile on the nonbearing surface against separation | 11.25° | 13.75° | 16.25° |
| ØD | Inside diameter at the open end of the female taper at a distance of IT from the opening | 3.400 | 3.430 | 3.460 |
| E | Depth of the female taper | 8.200 | 8.450 | 8.700 |
| ØG | Inside diameter of the smaller end of the female taper at a distance of Ω from the opening | 3.070 | 3.130 | 3.190 |
| ØH | Major outside lug/thread diameter | 6.120 | 6.220 | 6.320 |
| ØJ | Minor outside lug/thread diameter | 5.000 | 5.185 | 5.370 |
| K | Length of the connector | 8.600 | 8.900 | — |
| M | Width of the lug profile at the crest | 0.400 | 0.500 | 0.600 |
| (M) | Width of the thread profile at the crest (reference) | — | (0.787) | — |

TABLE 1-continued

Dimensions of a standard ISO 80369-6 Female Neuraxial Connector.
ISO 80369-6 Female Neuraxial Connector with Lugs

| Reference | Designation | Dimensions (mm) | | |
|---|---|---|---|---|
| | | Minimal | Nominal | Maximum |
| N | Width of the lug profile at the root at a diameter corresponding to ØJ maximum | 0.700 | 0.900 | 1.100 |
| N | Width of the thread profile at the root at a diameter corresponding to ØJ maximum | 0.890 | 0.995 | 1.100 |
| P | Pitch of the double-start, right-hand thread | 2.373 | 2.500 | 2.627 |
| R1 | Radius at the entrance of the female taper | 0.000 | 0.100 | 0.254 |
| S | Angle of the external thread profile on the bearing surface against separation | 11.25° | 13.75° | 16.25° |
| ØU | Inside diameter of the fluid lumen of the connector | — | 1.500 | 2.300 |
| V | Angle of the slope of the lug to be measured from a plane parallel with the tip of the connector | 11.0° | 13.0° | 15.0° |
| Y | Chord length at the base of the lug in a plane at a right angle to the axis of the connector | 4.100 | 4.250 | 4.400 |
| Ω | Distance from the opening to ØG | — | 6.500 | — |
| π | Distance from the opening to ØD | — | 0.500 | — |

FIG. 11 is a standard threaded male ISO 80369-6 neuraxial connector 2000, which is also referred to as an NRFit™ connector, dimensioned for compatibility with the misconnection mitigation benefits engineered into the ISO 80369 series of standards (ISO 80369-6:2016). The selectably locking male connector threaded sections 2130 and other correlated structures correspond with the values in Table 2 and are dimensionally compatible with the female range for the features of the technology, but actual parts, typically injection molded, may deviate outside these ranges. Table 2 values expressed as a dash, "-", represent boundless values. Each of the dimensions shown below can be applied to a male connector having the previously-described selectably locking features according to embodiments of the disclosure.

TABLE 2

Dimensions of a standard ISO 80369-6 Male Neuraxial Connector.
ISO 80369-6 Male Neuraxial Lock Connector

| Reference | Designation | Dimensions (mm) | | |
|---|---|---|---|---|
| | | Minimal | Nominal | Maximum |
| (a)† | Angle of taper (5% taper nominal) | — | (2.86°) | — |
| b | Angle of the internal thread profile on the nonbearing surface against separation | 11.25° | 13.75° | 16.25° |
| c† | Recess or protrusion of the tip | −0.400 | 0.000 | 0.400 |
| Ød† | Outside diameter at the tip of the male taper at a distance of IT from the tip of the male taper | 3.170 | 3.210 | 3.250 |
| e† | Length of the male taper | 8.130 | 8.380 | 8.630 |
| Øg† | Outside diameter of the larger end of the male taper at a distance of Ω from the tip of the male taper | 3.450 | 3.510 | 3.570 |
| Øj | Minor inside thread diameter | 5.420 | 5.520 | 5.620 |
| k† | Length of the connector | 8.000 | 8.300 | — |
| (m) | Width of the thread profile at the crest (reference) | — | (0.651) | — |
| n | Width of the thread profile at the root | 0.890 | 0.995 | 1.100 |
| p | Pitch of the double-start, right-hand thread | 2.373 | 2.500 | 2.627 |
| Øq | Major inside thread diameter | 6.750 | 6.925 | 7.100 |
| r1† | Radius at the outside tip of the male taper | 0.000 | 0.100 | 0.254 |
| r2† | Radius at the inside tip of the male collar (reference) | (0.000) | (0.100) | (0.254) |
| s | Angle of the internal thread profile on the bearing surface against separation | 11.25° | 13.75° | 16.25° |
| t | Distance from the tip of the connector to the start at the root of the first complete thread profile of the internal thread | — | 1.500 | 1.800 |
| Øu† | Inside diameter of the fluid lumen of the connector | — | 1.150 | 2.300 |
| Øz | Diameter of the smallest cylinder that encompasses the outside surfaces of the external features of the collar | 8.850 | 10.500 | 11.500 |
| Ω | Distance from the opening to ØG | — | 6.500 | — |
| π | Distance from the opening to ØD | — | 0.500 | — |

†Dimension not shown in figures connectors in Table 1. The dimensions shown below are for reference only and can be adapted to be dimensionally compliant with future updated standards. The dimensions shown in Table 2 are meant to quantify an ideal working FIGS. 12A-12D show a standard female ISO 80369-3 enteral connector 3000. Shown is a partially threaded version, as described with reference to FIGS. 7A and 7B, and dimensioned for compliance with ISO 80369-3:2016. FIG.

12A is a perspective view; FIG. 12B is a top view from the threaded end; FIG. 12C is a cross-sectional view; and FIG. 12D is a side view. The dimensions shown in Table 3 represent the dimensions specified in the most current version of ISO 80369-3 and are for reference only. Values expressed as a dash, "-", represent boundless values. The female connector shown in FIGS. 9A-9D complies with the dimensions in Table 3 below.

selectably locking male connector threaded sections 2130 and other correlated structures correspond with the values in Table 4 and are dimensionally compatible with the standard female connectors in Table 3. The dimensions shown below are for reference only and can be adapted to be dimensionally compliant with future updated standards. The dimensions shown in Table 4 are meant to quantify an ideal

TABLE 3

Dimensions of a standard ISO 80369-3 Female Enteral Connector.
ISO 80369-3 Female Enteral Connector

| Reference | Designation | Dimensions (mm) | | |
|---|---|---|---|---|
| | | Minimal | Nominal | Maximum |
| A | Angle of taper (6% taper nominal) | — | (3.44°) | — |
| C | Projection of the female taper from the thread start | 0.50 | 0.60 | 0.70 |
| ØD | Inside diameter at the open end of the female taper | 5.64 | 5.69 | 5.74 |
| E | Depth of the female taper | 7.04 | 7.14 | 7.24 |
| ØF3 | Outside diameter at the tip of the female taper | 6.80 | 6.90 | 7.00 |
| ØG | Inside diameter of the smaller end of the female taper at E from the opening of the female taper | 5.21 | 5.26 | 5.31 |
| ØH | Major outside thread diameter | 9.83 | 9.93 | 10.03 |
| ØJ | Minor outside thread diameter | 8.00 | 8.10 | 8.20 |
| M | Width of the thread profile at the crest | 0.80 | 0.90 | 1.00 |
| N | Width of the thread profile at the root | 1.65 | 1.75 | 1.85 |
| P† | Pitch of the double-start, right-hand thread | 2.45 | 2.50 | 2.55 |
| R3 | Length of clearance for male connector collar and threads | 6.90 | 7.00 | 11.00 |
| T3 | Angle at end of female taper | 40° | 45° | 50° |
| ØU | Inside diameter of the fluid lumen of the connector | — | 2.90 | 2.95 |
| ØW | Diameter of the smallest cylinder that encompasses the outside surfaces of the external features at R3 | 13.30 | — | — |
| X3 | Chord length of thread major diameter (ØH) at thread start | 0.25 | 0.50 | 1.50 |
| Y | Chord length at extremity of thread in a plane at a right angle to axis of the connector | 6.00 | — | — |
| Z3 | Face angle at thread start | — | — | 40° |

†Dimension not shown in figures

Figure 13A:
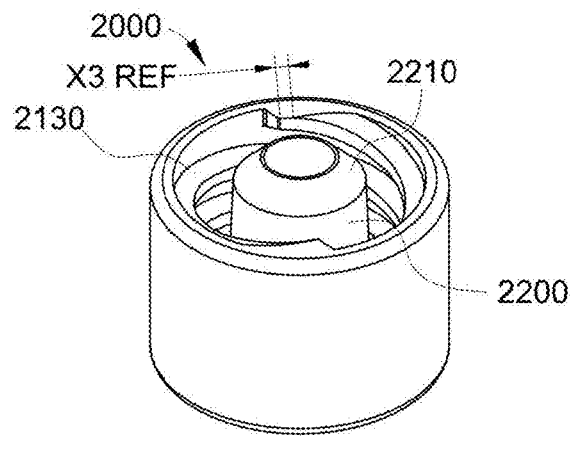
FIGS. 13A-13D are drawings of a male ISO 80369-3 enteral connector, according to various known embodiments.
Figure 13B:
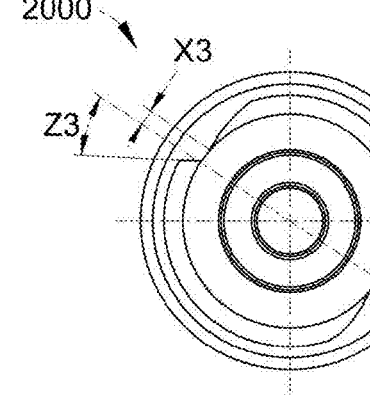
Figure 13C:
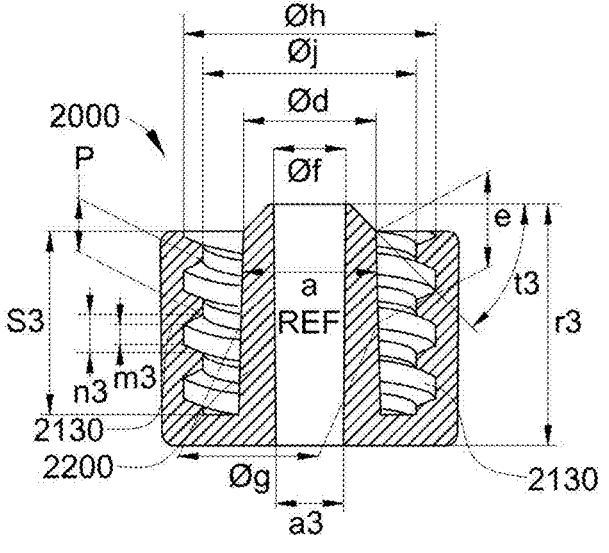
Figure 13D:
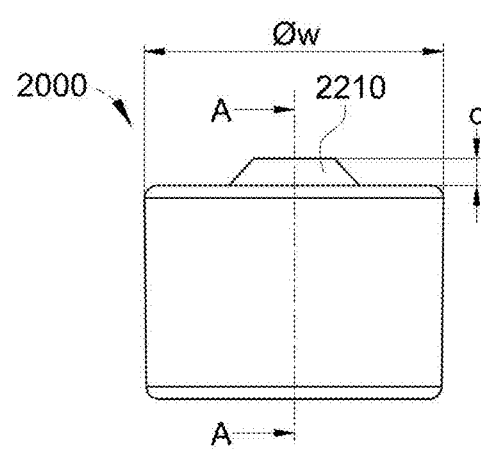

FIGS. 13A-13D are drawings of a standard male ISO 80369-3 enteral connector 2000, according to various example embodiments. FIG. 13A is a perspective view; FIG. 13B is a top view from the threaded end; FIG. 13C is a cross-sectional view; and FIG. 13D shows a side view. The depicted connector 2000 is dimensioned for compatibility with the misconnection mitigation benefits engineered into the ISO 80369 series of standards (ISO 80369-3:2016). The working range for the features of the technology, but actual parts, typically injection molded, may deviate outside these ranges. Values expressed as a dash, "-", represent boundless values. Each of the dimensions shown below can be applied to a male connector having the previously-described selectably locking features according to embodiments of the disclosure.

TABLE 4

Dimensions of a standard ISO 80369-3 Male Enteral Connector.
ISO 80369-3 Male Enteral Connector

| Reference | Designation | Dimensions (mm) | | |
|---|---|---|---|---|
| | | Minimal | Nominal | Maximum |
| (a) | Angle of taper (6% taper nominal) | — | (3.44°) | — |
| c | Projection of the tip of the connector nozzle | 0.50 | 0.60 | 0.70 |
| Ød | Outside diameter at the tip of the male taper | 5.36 | 5.41 | 5.46 |
| e | Length of the male taper (Ød to Øg) | 3.72 | 3.82 | 3.92 |
| Øf | Inside diameter at the tip of the male taper | 0.00 | 2.90 | 2.95 |
| Øg | Outside diameter at the larger end of the male taper at e from the tip of the male taper | 5.59 | 5.64 | 5.69 |
| Øh | Major inside thread diameter | 10.13 | 10.23 | 10.33 |
| Øj | Minor inside thread diameter | 8.55 | 8.65 | 8.75 |
| m3 | Width of the thread groove at the root | 1.05 | 1.15 | 1.25 |

TABLE 4-continued

Dimensions of a standard ISO 80369-3 Male Enteral Connector.
ISO 80369-3 Male Enteral Connector

| Reference | Designation | Dimensions (mm) | | |
|---|---|---|---|---|
| | | Minimal | Nominal | Maximum |
| n3 | Width of the thread groove at the crest | 1.80 | 1.90 | 2.00 |
| p | Pitch of the double-start, right-hand thread | 2.45 | 2.50 | 2.55 |
| s3 | Length of nozzle from end of collar | 6.82 | — | — |
| t3 | Angle of projection of nozzle from end of collar | 40° | 45° | 50° |
| Øw | Diameter of the smallest cylinder that encompasses the outside surfaces of collar's external features | 12.00 | 12.20 | — |
| x3 | Chord length of thread minor diameter (Øj) at thread start | 0.25 | 0.50 | 1.50 |
| Z3 | Face angle at thread start | — | — | 40° |

†Dimension not shown in figures

FIG. 14 is cross-sectional view of a standard male ISO 80369-7 intravenous/intravascular connector 2000 or Luer connector. The depicted connector 2000 is dimensioned for compatibility with the misconnection mitigation benefits engineered into the ISO 80369 series of standards (ISO 80369-7:2021). The selectably locking male connector threaded sections 2130 and other correlated structures correspond with the values in Table 5 and are dimensionally compatible with the female connectors in Table 6. The dimensions shown below are for reference only and can be adapted to be dimensionally compliant with future updated standards. The dimensions shown in Table 5 are meant to quantify an ideal working range for the features of the technology, but actual parts, typically injection molded, may deviate outside these ranges. Values expressed as a dash, "-", represent boundless values. Each of the dimensions shown below can be applied to a male connector having the previously described selectably locking features according to embodiments of the disclosure.

Figure 15D:
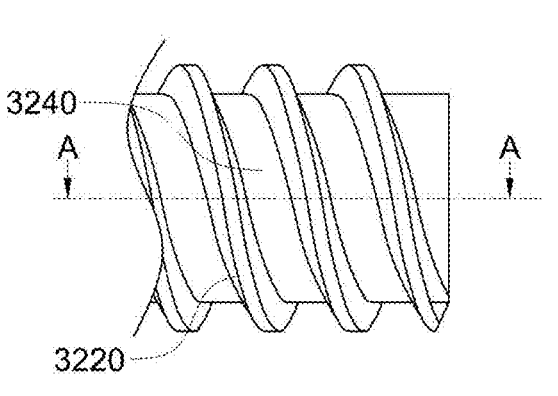
Figure 15E:
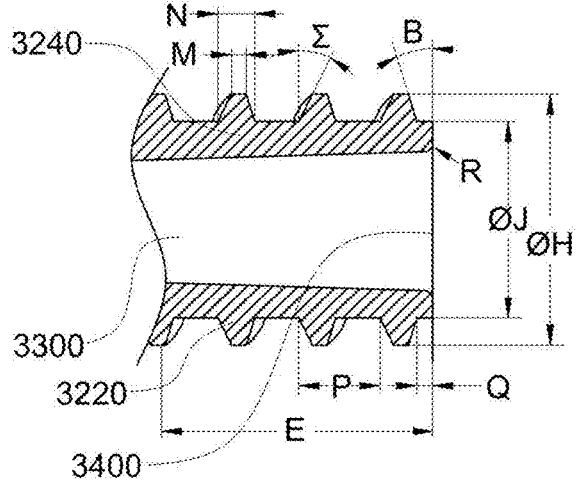

FIGS. 15A-15E are drawings of a standard female ISO 80369-7 intravenous/intravascular connector or Luer connector, according to various example embodiments. FIG. 15A is a top view from the threaded end; FIG. 15B is a side view showing the partial thread angle; FIG. 15C is a cross-sectional view; FIG. 15D shows the fully threaded version; and FIG. 15E is a cross-section of FIG. 15E. FIGS. 15A-15C are a partially threaded version, as described with reference to FIGS. 7A and 7B, but dimensioned for compliance with ISO 80369-7:2021 standards for misconnection mitigation; FIGS. 15D and 15E show a fully threaded version, as described with reference to FIGS. 6A and 6B, but dimensioned for compliance with ISO 80369-7:2021 standards for misconnection mitigation. The dimensions shown in Table 6 represent the dimensions provided in the most current version of ISO 80369-7 and are for reference only. Values expressed as a dash, "-", represent boundless values.

TABLE 5

Dimensions of a standard ISO 80369-7 Male IV Connector.
ISO 80369-7 Male Luer Connector

| Reference | Designation | Dimensions (mm) | | |
|---|---|---|---|---|
| | | Minimal | Nominal | Maximum |
| β | Angle of internal thread profile on the non-bearing surface against separation | 25.0° | 30.0° | (57.0°) |
| c | Projection of the tip of the connector nozzle | 2.100 | 2.150 | (2.573) |
| e | Length of the male taper | 7.500 | 8.400 | 10.500 |
| Øh | Major inside thread diameter | 7.900 | 8.000 | 8.100 |
| Øj | Minor inside thread diameter | 6.800 | 7.000 | 7.200 |
| m | Width of the thread profile at the crest | 0.300 | (0.326) | (0.674) |
| n | Width of the thread profile at the root | (0.627) | 0.875 | 1.000 |
| (p) | Pitch of the double-start, right-hand thread | — | (2.500) | — |
| σ | Angle of internal thread profile on the bearing surface against separation | 25.0° | 27.5° | 30.0° |
| t | Distance from the tip of the connector to the bottom of the first complete thread profile of the internal thread | (2.727) | 3.025 | 3.200 |
| Øw | Diameter of the smallest cylinder that encompasses the outside surfaces of collar's external features | 8.800 | 9.700 | 11.500 |

TABLE 6

Dimensions of a standard ISO 80369-7 Female IV Connector.
ISO 80369-7 Female Luer Connector

| Reference | Designation | Dimensions (mm) | | |
|---|---|---|---|---|
| | | Minimal | Nominal | Maximum |
| (α)† | Angle of the taper (6% taper nominal) | — | (3.44)° | — |
| β | Angle of external thread/lug profile on the non-bearing surface against separation | 0.0° | 15.0° | (53.0°) |
| c | Projection of the tip of the connector nozzle | 2.100 | 2.150 | (2.573) |
| ØD† | Inside diameter at the open end of the female taper at 0.75 from the opening of the female taper | 4.198 | 4.248 | 4.298 |
| E | Depth of the female taper | 7.500 | 8.400 | 10.500 |
| ØG† | Inside diameter of the smaller end of the female taper at 0.75 from the opening of the female taper | 3.793 | 3.843 | 3.893 |
| ØH | Major outside thread/lug diameter for the extent of the thread feature | 7.730 | 7.780 | 7.830 |
| ØJ | Minor outside thread/lug diameter (diameter at the thread/lug root) | 5.515 | 6.123 | 6.730 |
| ØJ† | Outside diameter of the female Luer slip connector of the smallest cylinder of depth of 5.5 from the face of the connector that encompasses the connector's external features | 6.000 | 6.356 | 6.730 |
| M | Width of the thread/lug profile at the crest | 0.300 | (0.420 & 0.659) | (0.967) |
| N | Width of the thread/lug profile at the root at a diameter corresponding to ØJ max (6.730) | (0.553) | 1.073 | 1.200 |
| N2 | Width of the lug profile at the root at a diameter corresponding to 6.730 on the trailing end of the lug as it is screwed into a male connector | (0.533) | 1.073 | 2.070 |
| (P) | Pitch of the double-start, right-hand thread | — | (2.500) | — |
| Q | Distance from the face of the connector to the base of the thread | 0.000 | 0.200 | 0.300 |
| R | Radius at the entrance of the female taper | 0.000 | 0.250 | 0.500 |
| Σ | Angle of external thread profile on the bearing surface against separation | 25.0° | 27.5° | 30.0° |
| X | Chord length at the base of the lug in a plane at a right angle to the axis of the connector | — | 3.400 | 3.500 |
| Y | Chord length at the extremity of the lug in a plane at a right angle to axis of the connector | 2.710 | 2.810 | — |

†Dimension not shown in figures

What is claimed is:

1. A selectably locking medical coupler for providing selectably locking coupling between a male small bore medical connector and a female small bore medical connector, the coupler comprising:

a body connecting a male end and a female end, the body comprising an interior surface comprising opposing threaded sections alternating with opposing unthreaded sections;

an internal bore extending from the male end through the female end;

the male end comprising a nozzle having a tapered end; and the female end positioned at an opposing side of the body from the male connector, wherein the male end is configured to couple with and is dimensionally compatible with a female connector, wherein the female end is configured to couple with and is dimensionally compatible with a male connector, wherein each of the opposing unthreaded sections has a width greater than or equal to a corresponding lug width of the female connector, wherein when the coupler is coupled with both the female connector and the male connector in a first position in which the opposing threaded sections mate with the lugs of the female connector, the coupler forms a threadably locking connection, wherein when the coupler is coupled with both the female connector and the male connector in a second position, the lugs of the female connector align with and slot into the unthreaded sections to form a breakaway connection, wherein the coupler remains fluidly coupled when selecting between the first position and the second position or between the second position and the first position, and wherein at least one of the unthreaded sections comprises a window such that an alignment of the lugs with the opposing threaded sections is visible, thereby providing a user with a visual indication of whether the coupler is in the first position or the second position.

2. The coupler of claim 1, wherein at least one of the unthreaded sections comprise faint threads.

3. The coupler of claim 1, wherein the body further comprises visual alignment indicators on an external surface.

4. The coupler of claim 1, wherein the coupler is disposable and blocks contamination from entering the male connector or female connector during fluid transfer.

5. The coupler of claim 1, wherein the coupler is dimensioned to prevent tubing misconnections between body systems.

6. The coupler of claim 1, further comprising a tethered closure, the tethered closure connected to the coupler at a first end by a tether and comprising a second end having a female connector with a closed lumen, wherein the tethered closure is configured to removably provide a sealing arrangement around the nozzle of the coupler's male end when the male end of the coupler is not connected to a female connector.

7. A selectably locking male connector comprising:

a first connection end;

a central nozzle at an opposing end from the first connection end;

a body positioned between the first connection end and the central nozzle, the body comprising an interior surface comprising opposing threaded sections alternating with opposing unthreaded sections, at least one opposing unthreaded section comprising a window, wherein the window is configured to receive a lug of a corresponding female partially threaded female connector; and a central bore extending from the first connection end through the central nozzle, wherein the selectably locking male connector prevents tubing misconnections between body systems.

8. The selectably locking connector of claim 7, the body further comprising at least one tactile feedback feature, wherein the tactile feedback feature controls an amount of separation force needed to disengage the connectors.

9. The selectably locking connector of claim 8, wherein the tactile feature comprises faint threads along the unthreaded sections.

10. The selectably locking connector of claim 8, wherein the tactile feature is selected from one or more of: faint threads along the unthreaded sections, a plurality of bumps along a leading edge of the unthreaded sections, a bowed geometry along a leading edge of the unthreaded sections, and at least one semi-flexible section along an interior wall of the body.

11. The selectably locking connector of claim 7, further comprising a tethered closure connected to the selectably locking connector at a first end by a tether, the tethered closure comprising a second end having a female connector with a closed lumen, wherein the tethered closure is configured to removably provide a sealing arrangement around the central nozzle.

12. A selectably locking connector system for fluid transfer comprising:

a male connector, the male connector comprising a first connection end, a central nozzle at a second end opposite the first connection end, a body positioned between the first connection end and the central nozzle, the body comprising an interior surface comprising opposing threaded sections alternating with opposing unthreaded sections, a window in at least one of the opposing unthreaded sections, and a central bore extending from the first connection end through the central nozzle; and a corresponding female connector, the female connector comprising a first connection end, a cylindrical body at a second end opposite the first connection end, wherein the body comprises a female receiver, and a central bore extending from the first connection end through the female receiver, wherein the nozzle of the male connector is dimensionally compatible with the female receiver, wherein the selectably locking male connector prevents tubing misconnections between body systems, and wherein a female lug is centered in the window when the male and female connectors are coupled in a breakaway connection.

13. The system of claim 12, wherein an external wall of the female connector's cylindrical body comprises opposing lugs and wherein each of the opposing unthreaded sections has a width greater than or equal to a width of a corresponding opposing lug, wherein the male and female connectors are coupled in a threadably locking connection when the male opposing threaded sections mate with the female lugs, wherein the male and female connectors are coupled in a breakaway connection when the male opposing unthreaded sections align with the female lugs, and wherein the connectors remain sealed when switched between the breakaway connection and the threadably locking connection or between the threadably locking connection and the breakaway connection.

14. The system of claim 12, wherein an external wall of the female connector's cylindrical body is fully threaded, wherein the male and female connectors are coupled in a threadably locking connection when the male opposing threaded sections mate with the female connector's threads, wherein the fully threaded cylindrical body prevents the breakaway connection.

15. The system of claim 12, wherein the female connector comprises opposing slots in a sidewall of the cylindrical body such that the body flexes inward during coupling.

16. The system of claim 12, wherein the female connector is integrally connected to a syringe.

\* \* \* \* \*